(12) United States Patent
Starr et al.

(10) Patent No.: US 11,120,900 B2
(45) Date of Patent: Sep. 14, 2021

(54) MEDICAL HOME REMINDER UNIT AND SYSTEM

(71) Applicant: Mylan, Inc., Morgantown, WV (US)

(72) Inventors: Eric Starr, Butler, PA (US); Molly Knewtson, Pittsburgh, PA (US); Benjamin Che, Canonsburg, PA (US)

(73) Assignee: Mylan Inc., Canonsburg, PA (US)

(*) Notice: Subject to any disclaimer, the term of this patent is extended or adjusted under 35 U.S.C. 154(b) by 535 days.

(21) Appl. No.: 15/898,945

(22) Filed: Feb. 19, 2018

(65) Prior Publication Data

US 2018/0315498 A1    Nov. 1, 2018

Related U.S. Application Data

(60) Provisional application No. 62/492,353, filed on May 1, 2017.

(51) Int. Cl.
| | |
|---|---|
| *G16H 20/13* | (2018.01) |
| *G16H 80/00* | (2018.01) |
| *A61J 7/04* | (2006.01) |
| *A61J 7/00* | (2006.01) |

(52) U.S. Cl.
CPC .......... *G16H 20/13* (2018.01); *A61J 7/0076* (2013.01); *A61J 7/0084* (2013.01); *A61J 7/0418* (2015.05); *G16H 80/00* (2018.01); *A61J 7/0481* (2013.01); *A61J 2200/30* (2013.01)

(58) Field of Classification Search
CPC ....... G16H 20/13; G16H 80/00; A61J 7/0418; A61J 7/0076; A61J 7/0084; A61J 7/0481; A61J 2200/30

USPC .......................................... 705/2–3
See application file for complete search history.

(56) References Cited

U.S. PATENT DOCUMENTS

| | | | |
|---|---|---|---|
| 8,391,104 B2* | 3/2013 | de la Huerga ... | G06K 19/07762 368/10 |
| 2002/0104848 A1* | 8/2002 | Burrows ............... | A61M 5/002 221/1 |
| 2006/0218015 A1* | 9/2006 | Walker .................. | A61J 7/0481 705/3 |
| 2008/0047178 A1 | 2/2008 | Marszalek | |
| 2009/0294521 A1* | 12/2009 | de la Huerga ... | G06K 19/07762 235/375 |
| 2011/0119090 A1* | 5/2011 | Lazar ........................ | A61J 1/14 705/3 |
| 2016/0026773 A1 | 1/2016 | Chu et al. | |
| 2017/0095405 A1* | 4/2017 | Afsarifard ............. | A61J 7/0472 |

* cited by examiner

*Primary Examiner* — Michael Tomaszewski

(57) ABSTRACT

A medication reminder system comprises a controller device operable to transmit and receive data representing a dosage regimen for the medication for use with a medication indicia. The medication indicia is configured to contact a container having the medication disposed within the container. The medication indicia includes a transmitter operable to send data to the controller device to provide or generate input data representing confirmation of adherence to the dosage regimen to the controller device, wherein the controller device is operable to display an indicator representing the dosage regimen or a parameter associated with the dosage regimen. Additional systems, a computer readable storage medium and methods are disclosed.

19 Claims, 19 Drawing Sheets

| Add New Patient | ✕ |

ⓘ Patient Information

| First Name | Last Name | Phone Number |
| Jim | Smith | 123-555-6789 |

⌨ Device Sync

Device Key

123456

⊘ Device key is valid!

SUBMIT

FIG. 7

Regimen 🖨         BACK

| ◉ Pantoprazole | M W F | ✏ 🗑 |
| ◎ Albuterol | M W F | ✏ 🗑 |
| ◉ Budesonide | M W F | ✏ 🗑 |

⊕

Add

FIG. 8

Add Regimen ✕

⊘ Medication

Enter the medication name or check Other/Multiple to enter a custom value in the Notes step

| Pantoprazole ✕ |   ☐ Other/Multiple

[BACK] [NEXT]

FIG. 9

Days of Week

Select the day of the week that this medication is taken

☐ As needed ☐ Every Day

☐ M  ☑ Tu.  ☐ W  ☑ Th.  ☐ F  ☑ Sa.  ☑ Su.

[BACK] [NEXT]

Times of Day

Select up to four times a day for the medication reminder

Time #1
6:00 am ▽         ⊕   RESET

Time #2
8:30 am ▽

[BACK] [NEXT]

FIG. 11

○ Medication Notes
Optional

Take with food.
_____

15/140

[BACK] [SUBMIT]

FIG. 12

Regimen 🖨

⊙ Pantoprazole          M W F  ✏ 🗑

⊙ Albuterol             M W F  ✏ 🗑

⊙ Budesonide            M W F  ✏ 🗑

⊕

Up Next: Pantoprazole

FIG. 13

| | TODAY | ALL |
|---|---|---|
| PART | | |
| | Notifications | |
| | ⓘ Assistance Requested<br>John Smith, 7:42 PM | |
| | CLEAR | |

FIG. 14

📋 Diary

John Smith ✕

📅 Today (3/21/17) ▾

3:14 PM
March 21st, 2017 ⊗    Albuterol MISSED

Budesonide TAKEN    ✓    3:10 PM
March 21st, 2017

Pantoprazole TAKEN    ✓    3:09 PM
March 21st, 2017

FIG. 15

Needs Follow-up | Based on last week of activity

| NON-ADHERENT | INCONSISTENT | DISCONNECTED |

Mary Chen    Last connected: Mar. 15th, 2017   [FOLLOW UP]

Bob Dole    Last connected: Mar. 15th, 2017   [FOLLOW UP]

Sally Brown    Last connecte...   Follow Up

John Smith
(123) 456-7890

Follow-up History
Last 5 attempts

↘ Unavailable
Feb 23rd, 2017

↗ Followed Up
Mar 8th, 2017

Percentage Taken
Past Month

Recently Missed
Last 7 days

Albuterol   76%    ☺ Albuterol   [2 DOSE]

Budesonide   83%    ☻ Budesonide   [2 DOSES]

Pantoprazole   56%    ☻ Pantoprazole   [3 DOSES]

↘ UNAVAILABLE    ↗ FOLLOWED UP

FIG. 17

⊘ Smart Dot (color & letter)

Attach a new Smart Dot to the pill bottle for Albuterol, then press the Smart Dot to confirm.

✓ Grey (As Needed) Smart Dot confirmed!

| BACK | NEXT |

Alert: Disconnected Patients

The patients listed below are disconnected and have medication reminders due in the next hour. Please contact patient immediately.

Disconnected Patients (3)

- Patient 16
- Patient 17
- Patient 18

Patient 16

🕐 Next-Up Reminder

℞ Atorvastatin    ⓘ DUE AT 12PM (42:12 remaining)

📞 (see data sheet)

🗓 Reminder Unit

~21 HOURS OFFLINE

Device Key: 123456
Last connected: 1:55PM on August 28th.
Status: Connection Lost

DISMISS

FIG. 24

MEDICAL HOME REMINDER UNIT AND SYSTEM

TECHNICAL FIELD

The present disclosure generally relates to a system that provides a medication regimen reminder and/or real time monitoring of medication doses taken by a patient.

BACKGROUND

Retail customers and/or patients can be engaged in a medical therapy, which may include diet, exercise and/or a prescription and/or a non-prescription medication dosing regimen, which may be employed to treat an illness. In some cases, hospitalized patients are often discharged and instructed by one or more medical practitioners to comply with a medical therapy.

Such medication dosing regimen can include one or a plurality of medications administered over a regimen, which may include one or more medications. The medication dosing regimen can require administration of medications simultaneously, at different times and/or according to days of a week or time of day. Such medication regimens may be administered in addition to existing medication regimens that a user may take for nutritional, therapeutic and/or illness treatment.

Such medication regimens, however, often suffer from poor patient adherence. In fact, many patients fail to adhere to their medication regimens. In some cases, life-style related medications may also suffer from poor user adherence. Factors that contribute to non-adherence may include complexity of medication regimen, patient failure in filling prescriptions, incorrect order and/or prescription, cost, adverse side effects, patient reluctance, lack of motivation, non-reconciliation with existing medication and/or patient physiological issues.

Various medications of a medication regimen can be dispensed from a medication container to a user with or without tamper resistance and without the monitoring of patient adherence. Multiple dose packaging can dispense a single medication according to a regimen including day, e.g., Monday, Tuesday, etc. and/or time of day. This disclosure describes an improvement over these technologies.

SUMMARY

In one embodiment, a medication reminder system is provided. The system comprises a controller device operable to transmit and receive data representing a dosage regimen for the medication for use with a medication indicia. The medication indicia is configured to contact a container having the medication disposed within the container. The medication indicia includes a transmitter operable to send data to the controller device to provide or generate input data representing confirmation of adherence to the dosage regimen to the controller device, wherein the controller device is operable to display an indicator representing the dosage regimen or a parameter associated with the dosage regimen.

In one embodiment, a computer-implemented method for providing a medication reminder is provided. The method comprises transmitting and receiving data representing a dosage regimen for the medication to and from a controller device for use with a medication indicia, the medication indicia configured to contact a container having the medication disposed within the container, the medication indicia including a transmitter operable to send data to the controller device; and providing or generating input data representing confirmation of adherence to the dosage regimen to the controller device.

In one embodiment, a computer readable storage medium is provided. The computer readable storage medium stores instructions that, when executed by a computer, cause the computer to: transmit and receive data representing a dosage regimen for a medication at the computer for use with a medication indicia, the medication indicia configured to contact a container having the medication disposed within the container, the medication indicia including a transceiver operable to send and receive data to and from the computer; and providing or generating input data representing confirmation of adherence to the dosage regimen to the computer and/or medication indicia. In some embodiments, the computer, the indicia, or both are operable to display an indicator representing the dosage regimen or a parameter associated with the dosage regimen.

In one embodiment, a medication reminder system is provided. The medication reminder system comprises a controller device; a set of adhesive medication indicia; a healthcare discharge portal web application with a medication regimen setup and adherence tracking features for hospitals; a caregiver controller device comprising a smartphone application with patient monitoring and adherence tracking features for caregivers; and a cloud network that performs as a scheduling engine and database for managing medication regimens and reminders for users of the medication reminder system.

In one embodiment, a medication reminder system is provided. The system comprises a controller device operable to transmit and receive data including a dosage regimen for the medication. The controller device having a display of a first set of medication indicia, each medication indicia representing the dosage regimen or a parameter associated with the dosage regimen. A second set of medication indicia including a transmitter operable to send data to the controller device. The second set of medication indicia corresponding to the dosage regimen or the parameter associated with the dosage regimen of the first set of medication indicia. The second set of medication indicia is paired to the first set of medication indicia, and the second set of medication indicia is configured to contact a container having the medication disposed within the container.

In one embodiment, a medication indicia is provided. The medication indicia comprises an element being disposed with a medication container and including a transmitter that communicates a medication dosage regimen with a controller device.

In one embodiment, a medication reminder system is provided. The system comprises a medication indicia comprising a transceiver operable to transmit and receive data to provide or generate input data representing confirmation of adherence to a dosage regimen. The medication indicia is configured to contact a container having the medication disposed within the container. The medication indicia is operable to display an indicator representing the dosage regimen or a parameter associated with the dosage regimen.

In one embodiment, a medication reminder system is provided. The system comprises a computer comprising a tablet computer or a smartphone operable to transmit and receive data representing a dosage regimen for the medication for use with a medication indicia. The medication indicia is configured to contact a container having the medication disposed within the container. The medication indicia includes a transmitter operable to send data to the computer to provide or generate input data representing confirmation of adherence to the dosage regimen to the computer.

In one embodiment, a medication reminder system is provided. The system comprises a controller device operable to provide or generate input data representing confirmation of adherence to a dosage regimen for use with a medication indicia. The medication indicia is configured to contact a container having the medication disposed within the container, and the medication indicia is a sticker. The controller device is operable to display an indicator representing the dosage regimen or a parameter associated with the dosage regimen.

BRIEF DESCRIPTION OF THE DRAWINGS

The present disclosure will become more readily apparent from the specific description accompanied by the following drawings, in which:

FIG. 7 is a screen shot of a step in the healthcare discharge portal when a patient is added to the managed patient list after the controller device is powered on;

FIG. 8 is a screen shot of a step in the healthcare discharge portal when the patient's individual medication schedule is set up;

FIG. 9 is a screen shot of a step in the healthcare discharge portal when the patient's individual medication schedule is set up;

FIG. 11 is a screen shot of steps in the healthcare discharge portal when the patient's individual medication schedule is set up;

FIG. 12 is a screen shot of a step in the healthcare discharge portal when the patient's individual medication schedule is set up;

FIG. 13 is a screen shot of a step in the healthcare discharge portal when the patient's individual medication schedule is set up;

FIG. 14 is a screen shot of the healthcare discharge portal displaying an alert when a volume button on the controller device is held down for three seconds or longer;

FIG. 15 is a screen shot of the healthcare discharge portal showing a patient's medication diary page;

FIG. 17 is a screen shot of the healthcare discharge portal showing the follow up display;

FIG. 19 is a screen shot of the caregiver controller device when a caregiver is logged on;

FIG. 24 is a screen shot of the healthcare discharge portal showing a notification that is displayed when a patient's controller device is disconnected from a selected cellular network;

Figure 1:
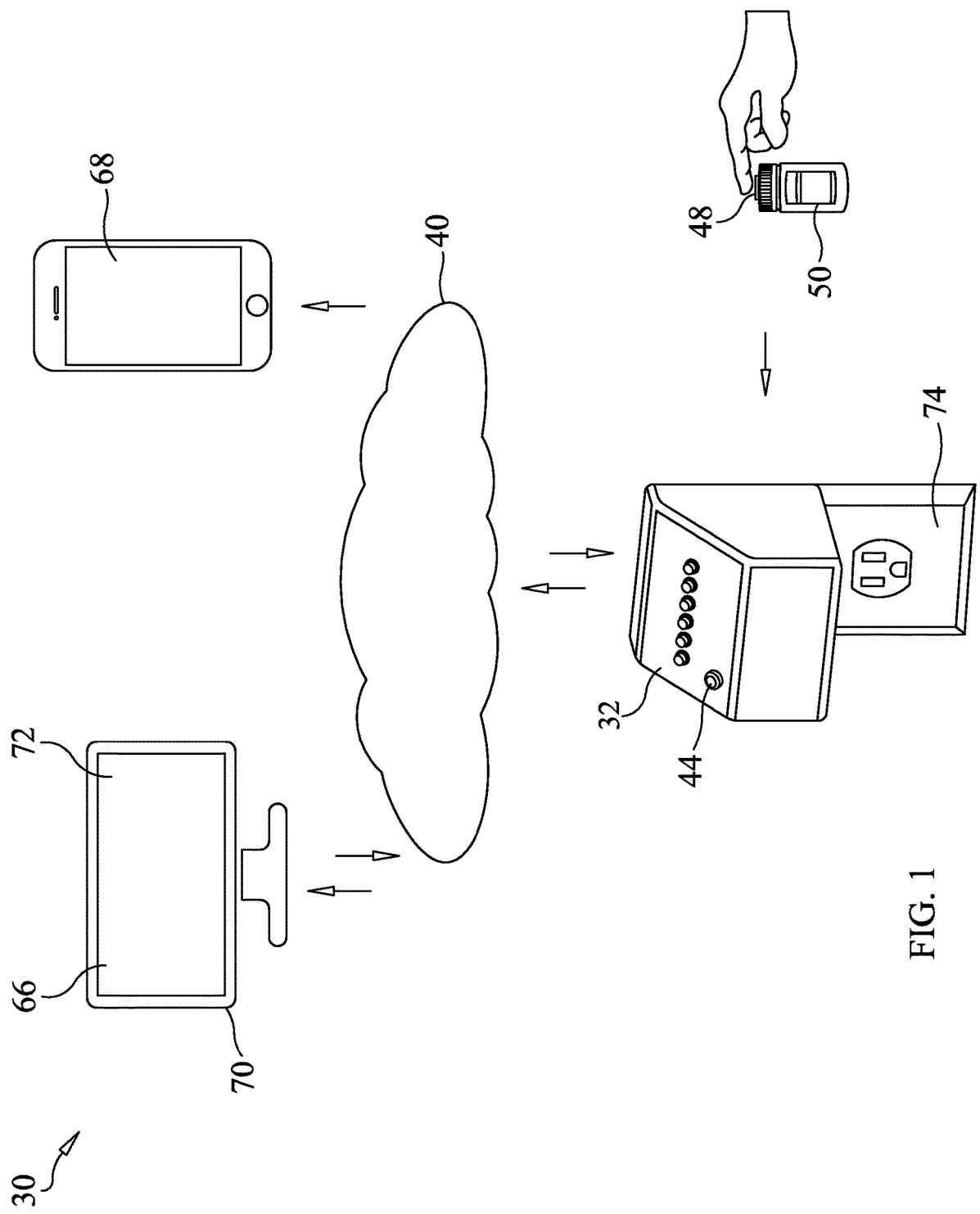
FIG. 1 is a schematic view of components of one embodiment of a system in accordance with the principles of the present disclosure.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

The exemplary embodiments of a medication reminder system and related methods of use disclosed are discussed in terms of reminder devices for the treatment of various diseases, illness and/or ailments and more particularly, in terms of a reminder device and system that provides a medication regimen reminder and/or real time patient monitoring. In some embodiments, the present system is employed with a computer-implemented method for providing a medication reminder. In some embodiments, the present system is employed with a computer readable storage medium.

In one embodiment, the present system is employed with a method such that a patient is discharged from a health care facility, such as, for example, a hospital after one or more diseases, illness and/or ailments and may be prescribed one or more medications. In some embodiments, a patient may be directed and/or prescribed medication, such as, for example, an anti-platelet agent, aspirin, a beta-blocker, an ACE inhibitor, an ARB statin, nitro-glycerin, a docusate and/or anti-depressants. In some embodiments, the present system is employed to avoid failure of a patient to adhere with such regimens and/or to take medications as prescribed or directed. In some embodiments, adherence failure can include the patient forgetting to take the prescribed medication and/or taking the medication at the incorrect time. In some embodiments, the present system is employed with a method for chronic dosing, for example, 30 day scripts. In some embodiments, the present system is employed with a method to facilitate adherence. In some embodiments, the present system is employed with a method for distribution of medication to a patient for treatment of one or more diseases, illness and/or ailments, such as, for example, pneumonia, heart failure, pain, infectious diseases that may include administration of medications, such as, for example, anti-retrovirals (ARV) for treatment of HIV/AIDS, dyslipidemia (high cholesterol), hypertension (high blood pressure), metabolic syndrome/insulin intolerance related to diabetes, psychological diseases and/or administration of transplant/anti-rejection drugs.

In some embodiments, the present system comprises a system that provides a medication regimen reminder and/or real time patient monitoring, and methods of use for storage, transportation and discharge of medications for the treatment of a medical condition. In some embodiments, the present system comprises a medication reminder system and methods of use for storage and discharge of medications including those for treating illnesses, such as, for example, elevated blood pressure, dyslipidemia (high cholesterol), diabetes, metabolic syndrome, heart failure, pneumonia, cardiac deficiencies, arthritis, illnesses in which pain is part of an on-going treatment plan, and/or life-style related medications such as, for example, birth control pills, hormone replacement pills and nutritional supplements, such as, for example, neutraceuticals, for example, having vitamin A, D, and E with a calcium supplement. In one embodiment, the systems and methods of the present disclosure are employed to aid a person with a medical condition requiring administration of multiple pills, doses or schedules as part of a regimen.

In some embodiments, the medication reminder system is partially or entirely packaged by a doctor, nurse or a pharmacist.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition may include administering one or more medications to a patient (human or other mammal). Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment includes, but is not limited to, reducing acute or chronic inflammation, inducing an anti-platelet effect, reducing hypertension, and lowering cholesterol.

In some embodiments, a biologically-active substance includes any substance or substances comprising a medicament, medication or drug including an active therapeutic substance, metabolite, hormone, steroid, vitamin, fatty acid, amino acid, sugar, carbohydrate, polypeptide or mineral. In some embodiments, a biologically-active substance includes any substance used for treatment, prevention, diagnosis, cure or mitigation of disease or illness. In some embodiments, a biologically-active substance includes any substance that affects anatomical structure or physiological function. In some embodiments, a biologically-active substance includes any substance that alters the impact of external influences on an animal, or metabolite thereof. In some embodiments, a complex dosage regimen includes a systematic administration of multiple dosage units at designated times during the day. In some embodiments, a dose includes each individual release of substance into body tissue.

The section headings are not meant to limit the disclosure and one section heading can be combined with other section headings.

Figure 2:
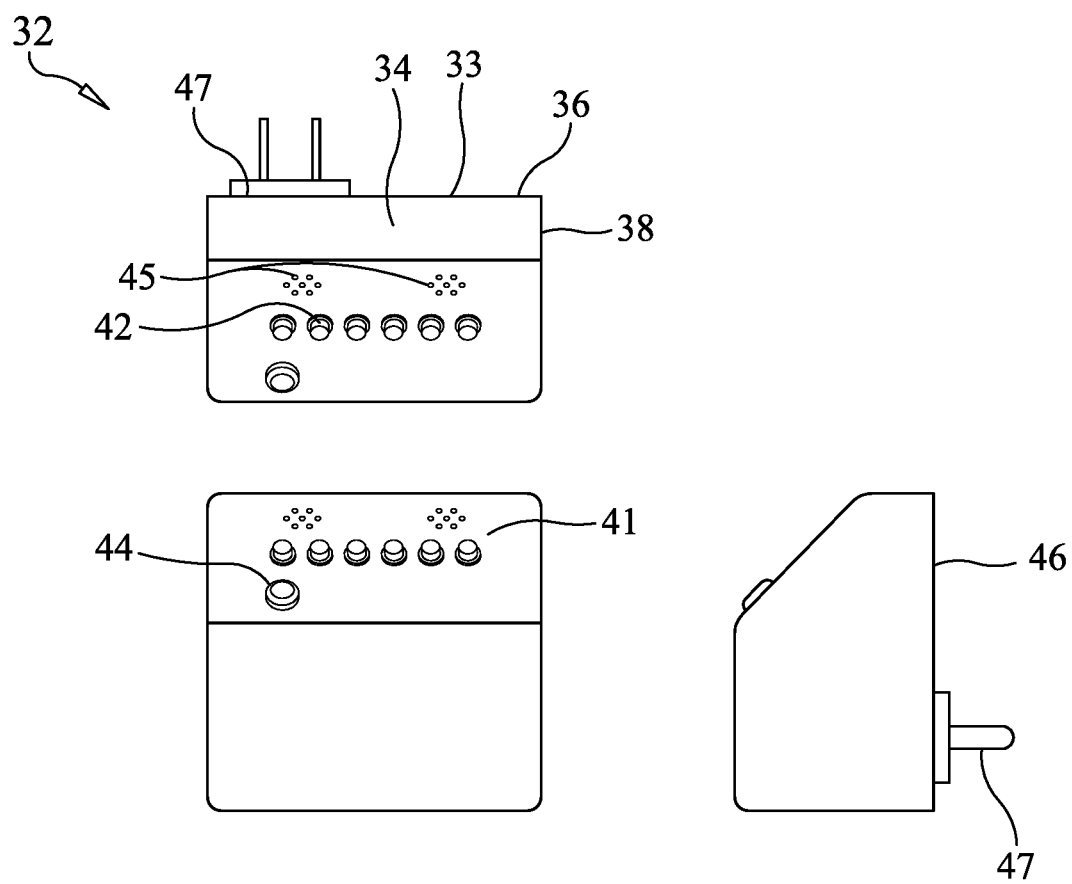
FIG. 2 is a top, front and side views of a controller device component of the system shown in FIG. 1.
Figure 3:
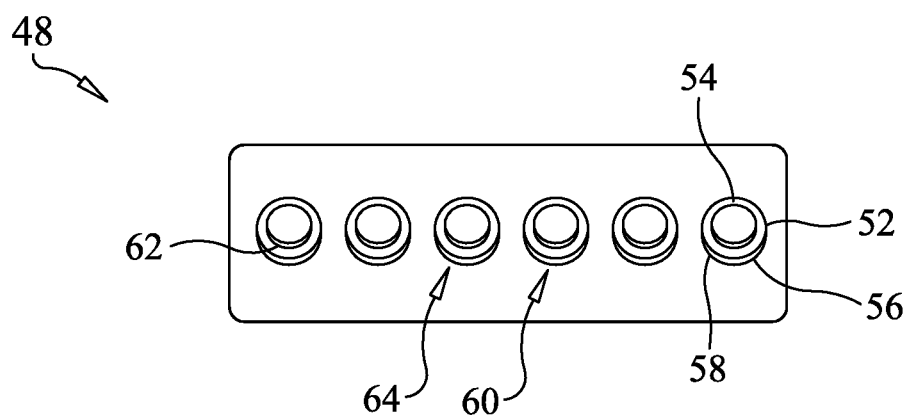
FIG. 3 is a top view of medication indicia components of the system shown in FIG. 1.

The following discussion includes a description of a medication reminder system including a controller device and medication indicia, related components and methods of employing the medication reminder system. Alternate embodiments are also disclosed. Reference is made in detail to the exemplary embodiments of the present disclosure, which are illustrated in the accompanying figures. Turning to FIGS. 1-3, there are illustrated components of a medication reminder system 30.

The components of medication reminder system 30, individually or collectively, can be fabricated from materials suitable for storage and dispensing of medication. In some embodiments, such materials include metals, ceramics, synthetic polymers such as thermoplastics, semi-rigid and rigid materials, elastomers, fabric and/or their composites. Various components of medication reminder system 30 may have material composites, including the above materials, to achieve various desired characteristics such as strength, rigidity, elasticity, adherence, and durability. The components of medication reminder system 30, individually or collectively, may also be fabricated from a heterogeneous material such as a combination of two or more of the above-described materials. The components of medication reminder system 30 may be monolithically formed, integrally connected or include fastening elements and/or instruments, as described herein.

Medication reminder system 30 is configured to increase medication adherence for recently discharged patients by enabling both customized medication reminders and real-time patient monitoring. Medication reminder system 30 can be used by healthcare practitioners such as, for example, doctors, nurses, a healthcare/medical practitioner; a caregiver such as a friend or a family member; and/or a patient.

Medication reminder system 30 includes a controller device 32 operable to transmit and receive data representing a dosage regimen for the medication for use with a set of medication indicia, as described below. Controller device 32 is operable to transmit and receive data to a healthcare discharge portal or a caregiver controller device, as described herein.

Controller device 32 includes a transceiver 33 comprising a wireless radio, such as, a Bluetooth® radio 34 and a microcontroller 36 used to receive and process data/transmissions from the set of medication indicia within a certain vicinity, as described herein. Controller device 32 includes a cellular modem 38 used for bi-directional data communication over a cellular telephone network with a cloud network 40. Controller device 32 is operable via cloud network 40. Cloud network 40 is a data network environment in which data from controller device 32 is stored in a network-attached storage, instead of being solely stored in a local storage.

Controller device 32 includes a display 41 having a set of medication indicia 42. Each medication indicia 42 represents a dosage regimen or a parameter associated with a dosage regimen selected by a healthcare/medical practitioner or caregiver. In some embodiments, set of medication indicia 42 can be an actuator. In one embodiment, set of medication indicia 42 is a series of six or more LED lights used as visual indicators, along with a buzzer used as an audio indicator. Set of medication indicia 42 may also include unique indicia comprising at least one color, letter, sound, light, and/or video. In some embodiments, each set of medication indicia 42 has a unique indicia that comprises at least one color, including, but not limited to red, blue, green, yellow, purple or white.

Controller device 32 includes a button 44 that is used primarily for volume control of speakers or buzzers 45. Controller device 32 includes a plug 47, such as an AC/DC adaptor. Controller device 32 comprises a unique identifier 46, such as a six digit alphanumeric string of characters printed on a label affixed to the back of controller device 32.

Medication reminder system 30 includes at least one or a plurality of medication indicia, such as a set of medication indicia 48 configured to contact at least one container 50 having the medication disposed therein. Set of medication indicia 48 can be universally applied to any type of container 50, as described herein. Set of medication indicia 48 is also configured to interact with set of medication indicia 42. Set of medication indicia 48 is paired with and corresponds to the dosage regimen or the parameter associated with the dosage regimen of set of medication indicia 42. For example, set of medication indicia 42 is wirelessly paired or autopaired to set of medication indicia 48 using a unique identifier, as described herein.

In some embodiments, set of medication indicia 48 can be an electronic button. Each set of medication indicia 48 includes a transmitter 52 comprising a wireless radio, such as, a Bluetooth® radio 54 and a microcontroller 56 used to send data/transmissions to controller device 32. In some embodiments, each set of medication indicia 48 can alternatively include a transceiver including transmitter 52 to send and receive data/transmissions to and from controller device 32.

Each set of medication indicia 48 includes a button 58 mounted on top of a circuit board 60 that records downward forces applied to each set of medication indicia 48, such as when a user presses on each set of medication indicia 48. Each microcontroller 56 is assigned a unique hardware identifier, such as, a six-byte wireless device address, also known as a media access control (MAC) address that is broadcasted alongside a numbered color code that corresponds to a color of set of medication indicia 48. Each set of medication indicia 48 includes a covering 62 that can be made from silicone. Each set of medication indicia 48 has a unique indicia that comprises at least one color, letter, sound, light and/or video. In some embodiments, set of medication indicia 48 has a unique indicia that comprises at least one color, including, but not limited to red, blue, green, yellow, purple or white. In some embodiments, a company identifier can be associated with the MAC address, the medication indicia 48 and/or the medication reminder system 30.

Each set of medication indicia 48 comprises an adhesive 64 affixed to the bottom surface of each of the set of medication indicia 48 to contact container 50 for adhesion. It will be understood that set of medication indicia 48 can contact container 50 by other means such as, for example, friction fitting, clip, magnet, threaded cap, or other contact means to keep set of medication indicia 48 with container 50.

Each set of medication indicia 42 corresponds to a particular medication, and each set of medication indicia 48 corresponds to the particular medication and the parameter associated with the dosage regimen. The parameter associated with the dosage regimen is at least one of the name of the particular medication, the time interval for administering the particular medication, strength of the particular medication, the dosing frequency of the particular medication, the dosage form of the particular medication, the route of administration of the particular medication, the patient's name or an alert for the particular medication.

Medication reminder system 30 includes a healthcare discharge portal 66 and a caregiver controller device 68. Healthcare discharge portal 66 transmits and receives data with controller device 32. Healthcare discharge portal 66 can be a web application with medication regimen setup and adherence tracking features for hospitals. Patients enrolled in a medication reminder program are set up with a patient profile in healthcare discharge portal 66 which stores information on their specific medication schedules. These patients are given a controller device 32 and a set of medication indicia 48 that are each attached to one or more containers 50 that are synced to the patient profile by a healthcare/medical practitioner.

Caregiver controller device 68 receives data with healthcare discharge portal 66 and controller device 68. In some embodiments, caregiver controller device 68 receives and transmits data with healthcare discharge portal 66 and controller device 68. Caregiver controller device 68 can be a smartphone application with patient monitoring and adherence tracking features for caregivers. Caregiver controller device 68 can also be a tablet computer application or a personal digital assist (PDA) application. The components of medication reminder system 30 are shown in the FIGS. In some embodiments, medication reminder system 30 can have a processor and memory to store, send and receive data, and to generate alerts based on such data.

Healthcare discharge portal 66 can be accessed through a computer 70. Computer 70 includes a computer readable storage medium 72 which stores instructions that, when executed by computer 70, cause computer 70 to transmit and receive data representing a dosage regimen for a medication at computer 70 for use with controller device 32 and set of medication indicia 48. Transmitter 52 of set of medication indicia 48 is operable to send data to controller device 32. Controller device 32 then transmits data to cloud network 40 and cloud network 40 then transmits the data to computer 70. The data transmitted to set of medication indicia 48 represents a dosage regimen for the medication. Input data is then provided or generated that represents a confirmation of adherence to the dosage regimen to computer 70 and/or set of medication indicia 48.

In some embodiments, computer readable storage medium 72 can include, but is not limited to any one or more of the known storage devices or systems (e.g., random access memory (RAM), read only memory (ROM), hard disk drive (HDD), floppy drive, zip drive, compact disk-ROM, DVD, bubble memory, redundant array of independent disks (RAID), network accessible storage (NAS) systems, storage area network (SAN), content addressed storage (CAS), and may also be one or more memory devices embedded within a CPU, or shared with one or more of the other components, and may be deployed locally or remotely relative to one or more components interacting with the memory or one or more modules.

Medication reminder system 30 includes cloud network 40. Cloud network 40 performs as a communication network or conduit that connects a network-attached storage device, such as a server to controller device 32 and/or computer 70. The server performs as a scheduling engine and database for managing medication regimens and reminders for the users of medication reminder system 30. Cloud network 40 via a web portal hosted on the server connects to cloud 40 to control a patient's controller device 32, triggering unique indicia, such as color-coded, audio-visual medication reminders from set of medication indicia 42 on controller device 32 as previously scheduled. In some embodiments, feeding adherence activity is also collected from set of medication indicia 48 back to cloud network 40 where it is then used to facilitate and inform (via aggregated data reports and individual adherence activity logs) targeted interventions by a healthcare/medical practitioner.

Controller Device Initialization, Pairing and Medication Indicia Syncing

Figure 4:
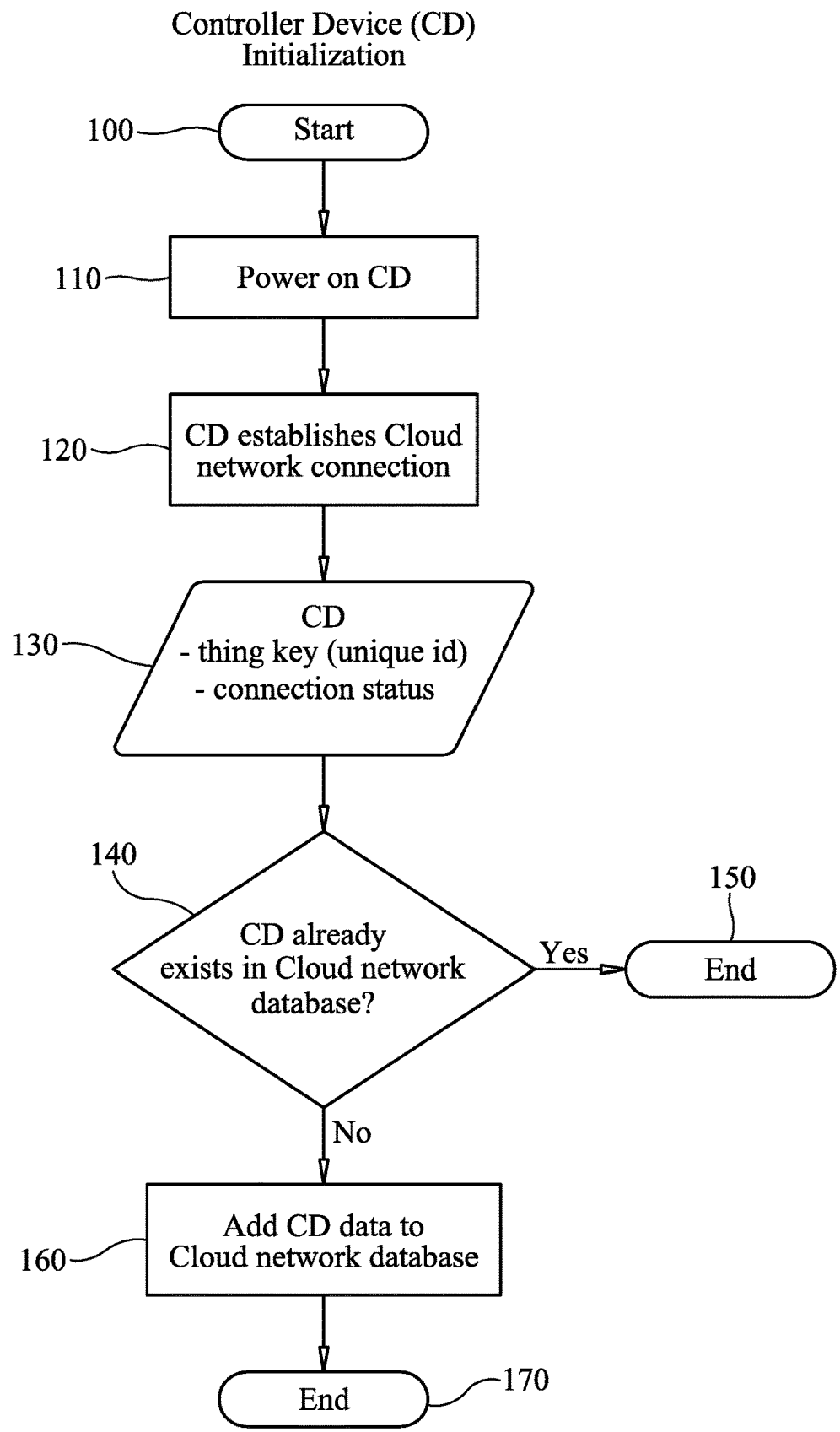
FIG. 4 is a flow chart of an initialization process of the system shown in FIG. 1. In some embodiments, the system is set up for individual patients by a healthcare/medical practitioner upon discharge. In some embodiments, the process begins when the healthcare/medical practitioner plugs a controller device into an accessible power outlet which accesses a healthcare discharge portal web application and creates a new patient profile for the patient being discharged. In some embodiments, the controller device will attempt to establish a cellular connection to a cloud network when powered on. If successful, it will alert the healthcare/medical practitioner, for example, by playing a buzzer tune and LED light sequence to confirm its connectivity to the network and will initialize itself in the cloud network if it has not been previously registered.

Medication reminder system 30 can be activated for individual patients by a healthcare/medical practitioner upon discharge. Controller device 32 initialization, as shown in the flow chart of FIG. 4 starts (100) when the healthcare/medical practitioner powers on controller device 32 (110) by inserting plug 47 into an accessible power outlet 74. The healthcare/medical practitioner then accesses healthcare discharge portal 66 for example, via computer 70, and creates a new patient profile for the patient being discharged. Controller device 32 will attempt to establish a connection (120) to cloud network 40 when powered on. If successful, it will play a buzzer tune and LED light sequence to confirm connectivity (130) to the network and will initialize itself in cloud network 40 if it has not been previously registered (140)-(170).

Figure 5:
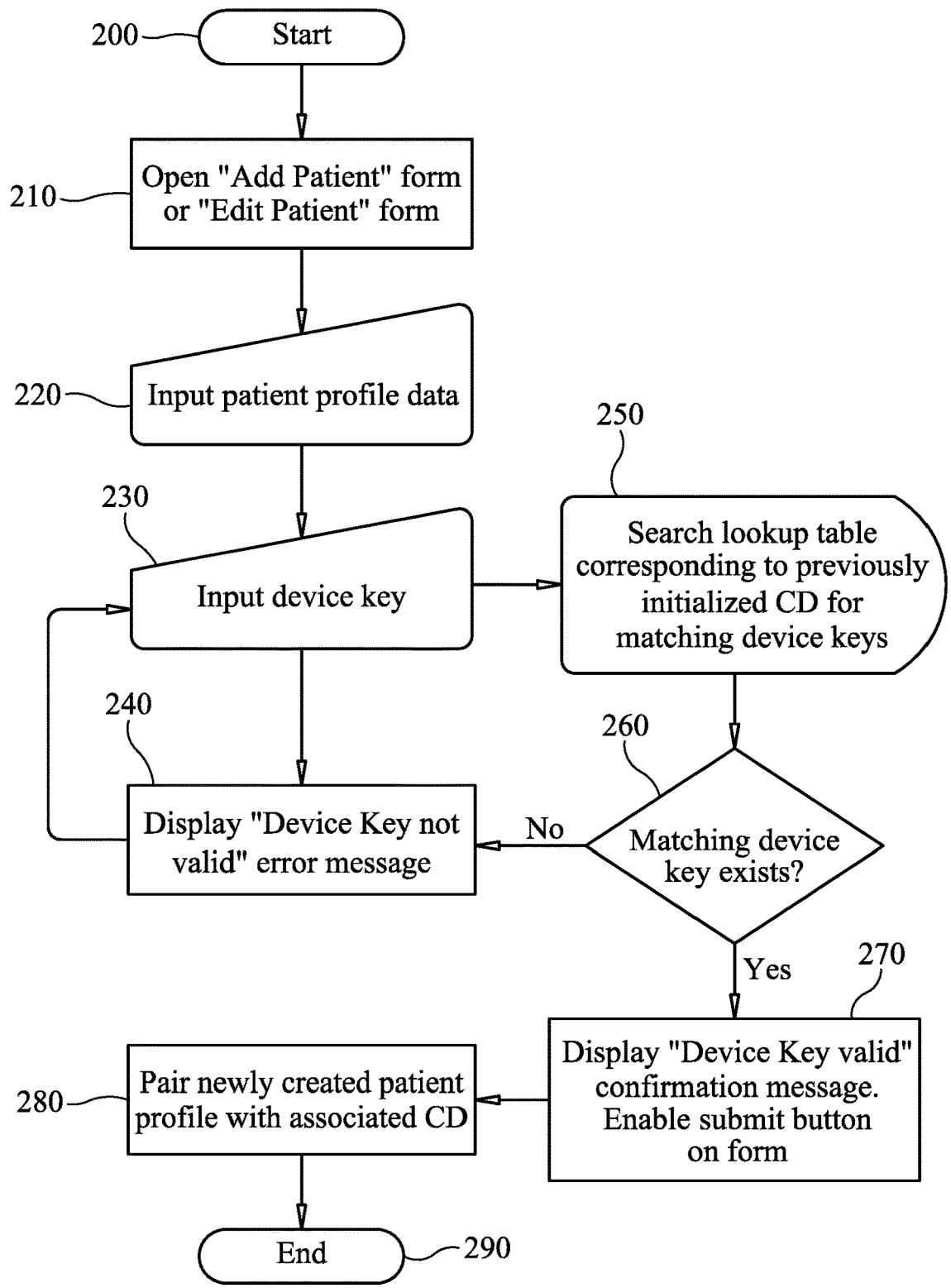
FIG. 5 is a flow chart of a controller device pairing. Following the flow chart of FIG. 4, in some embodiments, the healthcare/medical practitioner can then proceed to associate the newly connected controller device with the patient being discharged by entering the device's unique identifier in the healthcare discharge portal as an attribute in the patient's profile. Once this association is made, the healthcare/medical practitioner can begin configuring the patient's medication reminder schedules.

As shown in the flow chart of FIG. 5, the healthcare/medical practitioner can proceed to associate the connected controller device 32 with the patient being discharged by entering the controller device's unique identifier 46 in healthcare discharge portal 66 as an attribute in the patient's profile. Once this association is made, the healthcare/medical practitioner can begin configuring the patient's medication reminder schedules (200). For example, the healthcare/medical practitioner opens an "add patient" form or "edit patient" form (210). Next, the patient profile data is inputted (220) into an input device key (230). A table corresponding to previously initialized controller device 32 for matching device keys is searched/looked-up (250). If a matching device key exists (260), then a confirmation message "device key valid" is displayed, and a submit button on the form is enabled (270). The newly created patient profile is then paired with the associated controller device 32 (280). The pairing is then complete (290). If the matching device key does not exist (260), then an error message "device key not valid" is displayed (240).

The medication reminder schedules for a particular patient are configured individually for each of the medications prescribed as a part of the patient's medication regimen upon discharge. To reduce the rate of incorrect reminder configurations, a number of unique data confirmation methods are used. The first step of the configuration process requires the healthcare/medical practitioner to pick up container 50 of the medication that the reminder is being configured for and enter the medication name for that particular medication into the "configuration form" in healthcare discharge portal 66 user interface. An option titled "other/multiple" is also provided to indicate alternative drug delivery devices in place of a medication name associated with a container 50.

The next step involves taking a new individual set of medication indicia 48 and affixing it to an individual container 50 while the "add patient" or "edit patient" form is open in the healthcare discharge portal 66. While affixing individual set of medication indicia 48 to a container 50, the healthcare/medical practitioner will depress button 58 on the individual set of medication indicia 48, which then broadcasts a Bluetooth® transmission ("advertisement") containing the individual set of medication indicia's 48 unique hardware identifier (wireless device address/MAC address) as well as its color code. This unique hardware identifier and corresponding parameter associated with the dosage regimen being configured by the healthcare/medical practitioner is stored to compare to each time the individual set of medication indicia is pressed.

Bluetooth® radio 34 embedded in controller device 32 continually scans for incoming advertisements while controller device 32 is powered on. Software in the embedded microcontroller 36 is programmed to ignore incoming Bluetooth® advertisements from an individual set of medication indicia 48 unless the unique hardware identifier and corresponding parameter associated with the dosage regimen included in the broadcast matches the unique identifier and dosage regimen parameter stored previously. If no unique device identifier associated with the dosage regimen parameter broadcast by individual set of medication 48 have been stored, the controller device 32 plays an error buzzer tune.

As described above, when an individual set of medication indicia 48 is pressed for the first time, controller device 32 communicates the newly affixed individual set of medication indicia's 48 unique identifier to cloud network 40 where it is stored in the patient's data profile. Every time a controller device 32 connects to cloud network 40, it retrieves the latest list of saved unique hardware identifiers that it is associated with, which allows it to recognize individual set of medication indicia 48 input from previously synced individual set of medication indicia 48. The sync confirmation process is also reflected in computer 70 via healthcare discharge portal 66.

When an individual set of medication indicia 48 is pressed for the first time, controller device 32 stores the newly affixed individual set of medication indicia's 48 unique identifier on the device, locally, via flash or other storage medium. In some embodiments, other storage medium includes, but is not limited to, any one or more of the known storage devices or systems (e.g., random access memory (RAM), read only memory (ROM), hard disk drive (HDD), floppy drive, zip drive, compact disk-ROM, DVD, Blue-ray Disc™, bubble memory, redundant array of independent disks (RAID), network accessible storage (NAS) systems, storage area network (SAN), content addressed storage (CAS), and may also be one or more memory devices embedded within a CPU, or shared with one or more of the other components, and may be deployed locally or remotely relative to one or more components interacting with the memory or one or more modules.

In some embodiments, this stored unique hardware identifier can be reassigned. When button 44 on controller device 32 is depressed for a specific length of time, the software in the embedded microcontroller 36 plays a buzzer tune and LED light sequence for a preset duration of time, during which the device is placed in a "reassignment ready" state. While in this state, the first incoming Bluetooth® advertisement from an individual set of medication indicia 48 will be accepted and the unique hardware identifier in the incoming advertisement will replace the previously stored unique hardware identifier that matches the corresponding dosage regimen parameter. This state will expire at the end of the preset duration of time or after the first incoming advertisement is received, whichever comes first. This state can be triggered remotely by cloud network 40 when the healthcare/medical practitioner opens the "add patient" or "edit patient" form in healthcare discharge portal 66. Multiple controller devices within Bluetooth® proximity of each other cannot simultaneously enter this state due to a lock broadcast by the Bluetooth® radio 34 and enforced by the software in embedded microcontroller 36 on both controller devices. This feature is intended to accommodate the use of the system by multiple patients within the same Bluetooth range of each other (for example, while in the same house). Without this feature, controller device 32 cannot distinguish between set of medication indicia 48 feedback and feedback coming from other set of medication indicia 48 in the vicinity while being reassigned.

When a new individual set of medication indicia 48 is affixed and associated with the patient and his or her controller device 32, its color code is automatically populated into the medication reminder setup form, giving the healthcare/medical practitioner additional visual confirmation on computer 70 that the individual set of medication indicia 48 with the corresponding color has been linked to the medication name previously entered. If an out of range and unrecognized individual set of medication indicia 48 transmission was received by controller device 32, healthcare discharge portal 66 will display a warning message via computer 70 that suggests bringing the newly affixed individual set of medication indicia 48 and container 50 closer to controller device 32 to reconfirm the sync. The flowchart of FIG. 6 outlines this process.

Figure 6:
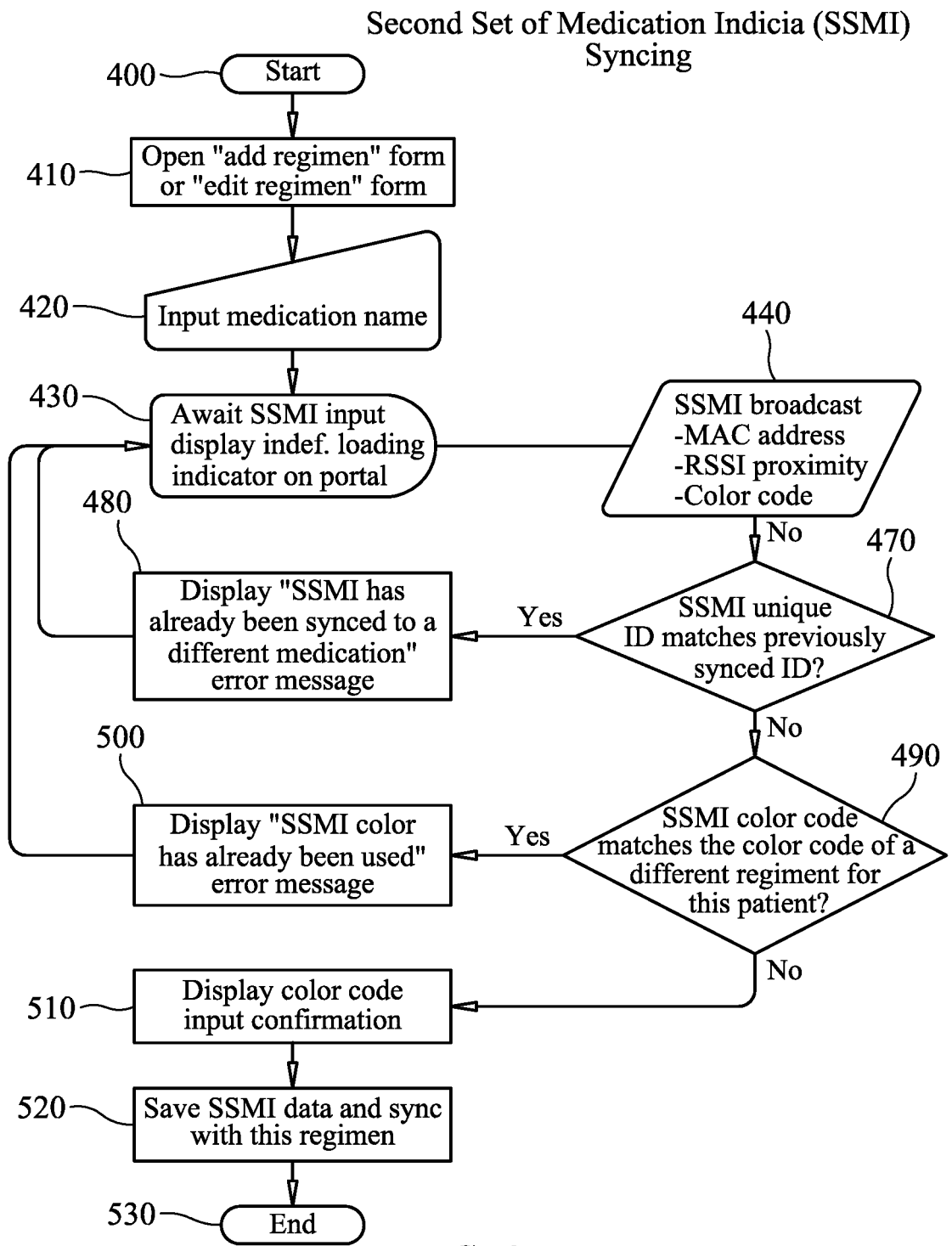
FIG. 6 is a flow chart of the medication indicia syncing process. In some embodiments, the sync confirmation process is also reflected in the user interface of the healthcare discharge portal. When a new medication indicia is affixed and associated with the patient and his or her controller device, its color code is automatically populated into a medication reminder setup form, giving the healthcare/medical practitioner additional visual confirmation on the user interface that the medication indicia with the corresponding color has been linked to the medication name previously entered. If an out of range and unrecognized medication indicia transmission was received by the controller device, the healthcare discharge portal user interface will display a warning message that suggests bringing the newly affixed medication indicia and medication container closer to the controller device to reconfirm the sync.
Figure 10:
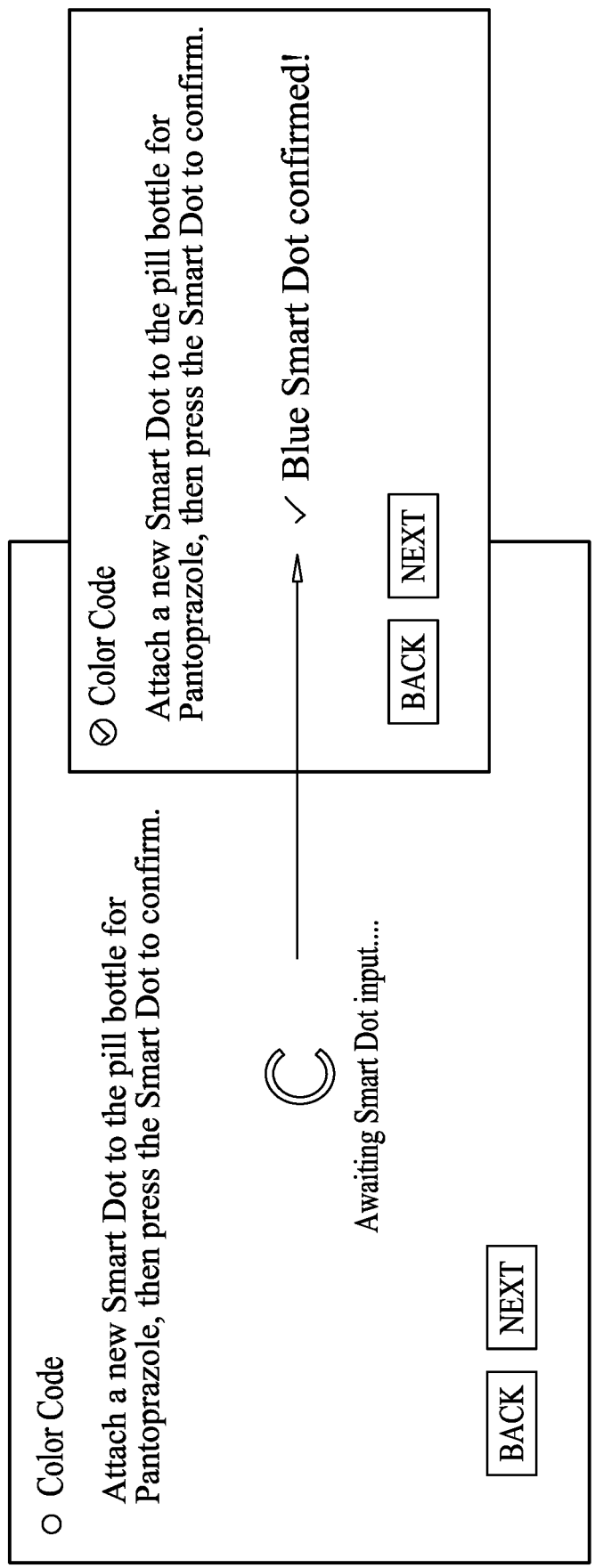
FIG. 10 is a screen shot of a step in the healthcare discharge portal when the patient's individual medication schedule is set up.

For example, in FIG. 6, the healthcare/medical practitioner starts the syncing process (400) by opening an "add regimen" form or "edit regimen" form in healthcare discharge portal 66 (410). Next, the medication name is inputted (420). Input from individual set of medication indicia 48 is awaited and an indefinite loading indicator on healthcare discharge portal 66 is displayed (430). Individual set of medication indicia 48 broadcasts (440) and a query is asked if individual set of medication indicia's 48 unique identifier matches a previously synced unique identifier (470). If yes, then an error message is displayed saying "individual set of medication indicia has already been synced to a different medication" (480). If no, then a query is asked if individual set of medication indicia's 48 color code matches the color code of a different regimen for this patient (490). If yes, then an error message is displayed stating "individual set of medication indicia color has already been used" (500). If no, then a color code input confirmation is displayed (510), the individual set of medication indicia 48 data is saved and synced with this regimen (520) and the syncing ends (530).

The final steps of the medication reminder process are done exclusively in the healthcare discharge portal 66 and involve configuring the days of the week and up to four times a day spaced two hours apart for the medication reminder. These time and date options can be skipped by selecting the "as needed" option, which saves that particular medication to the patient's profile but does not trigger any reminders. An optional medication notes field is also available.

Reminder Scheduling System

Once a patient's profile and associated medication reminder schedules are configured in healthcare discharge portal 66 web application, the data is persisted to a database in cloud network 40 and parsed by a reminder scheduling engine. This engine runs continuously in the cloud hosted server and acts as a controller of all actively connected controller devices 32 in the patients' homes. A state representation of the on/off status of the LEDs and buzzer (set of medication indicia 42) on each controller device 32 is stored and managed by this engine. When a particular medication or set of medications are due to be taken, the engine calculates a new LED/buzzer state representation (with the red LED adjusted to an "ON" status if the corresponding medication is due, for example) and adds this information to the update queue, which is processed and sent down via cellular connection to every controller device 32 that needs an update every 30 minutes on the hour.

Controller device 32 will turn on its LEDs and buzzer according to the state representation it has just received from the reminder scheduling engine, prompting the patient to take the medication corresponding to the active colors. The patient will then press the set of medication indicia 48 affixed to containers 50, triggering a Bluetooth® transmission to controller device 32. The set of medication indicia 48 will send data to controller device 32 to provide or generate input data representing confirmation of adherence to the dosage regimen to controller device 32. If the transmission is from a valid individual set of medication indicia 48 and its color code matches the color of a currently active LED, the LED is turned off. In some embodiments, Bluetooth® radio 54 and a microcontroller 56 of each set of medication indicia 48 are put to sleep in between data transmissions to conserve and/or extend battery life. Once each set of medication indicia 48 is pressed, it activates for a period of time, such as, for example, about 1 to about 10 seconds, to transmit the confirmation adherence data to controller device 32. Note that controller device 32 now has a different state representation as it just updated the LED on/off status on the controller device 32 side. This local state representation is preserved until controller device 32 next receives an update from cloud network 40. The color code of the individual set of medication indicia 48 associated with the medication that was just taken, however, is sent immediately to cloud network 40. The reminder scheduling engine logs this input and uses it for adherence logging. The engine also reconciles this data back into its update queue, preventing state representation conflicts. This reconciliation algorithm also records missed medication doses as well as allowing for a patient to take a medication ahead of the reminder without having the reminder for that particular medication to trigger after the fact.

Real-Time Data & Platform Extensibility

Medication reminder system 30 is configured with real-time data synchronization in medication-adherence data collected from the individual set of medication indicia 48 and controller device 32. The data is time stamped and communicated in near real-time to cloud network 40 over a cellular data connection, where it is reflected in the front-end applications (e.g., healthcare discharge portal 66 and caregiver controller device 68) without the need for a browser refresh or an application reload. This level of granularity in collected adherence data is leveraged with customized treatment and adherence programs that can be built on top of the medication reminder system 30 platform. In one embodiment, a program having logic to cause the computer to track movement of the user wearing a device is provided. Such program can be, for example, a tremor tracker that is used as an additional component to the medication reminder system 30 that requires an additional wearable device affixed to a patient suffering from Parkinson's disease or a related condition. The wearable device tracks the severity of a patient's tremors by taking readings from an in-built accelerometer and communicates these readings back to the patient's previously synced controller device 32. This data can then be accessed by a doctor and used to more effectively titrate the patient's medications, for example, increasing the amount of time between when a dose is taken and when the tremors return by increasing the dosage prescribed. It also can be used in conjunction with the medication reminder system to monitor patient compliance with the medication.

Usage Flow

Medication reminder system 30 usage can be grouped into functional categories based on three steps of use. The first step of use is discharge where a healthcare/medical practitioner on-boards new patients upon discharge from the hospital. The second step of use is home use. Home use is where a patient takes medication reminder system 30 home and uses medication reminder system 30. The third step is follow-up. Follow-up is when care coordinators identify non-adherent patients for further follow-up.

Healthcare Discharge Portal Setup

Medical reminder system 30 disclosed above is set up in the following manner as shown by FIG. 7. A medical practitioner, such as, for example, a healthcare/medical practitioner begins setup of the medical reminder system 30 by powering on a new controller device 32. Once powered on and connected to cloud network 40, controller device 32 will play a device connected tune and LED light sequence. The patient can now be added to the managed patient list via the "add patients" button on the patient's page of healthcare discharge portal 66, as shown in FIG. 7. One of the form fields required is the "device key" or unique identifier 46 which is an alphanumeric six digit code printed on the back of each controller device 32. Upon creating a patient in healthcare discharge portal 66, controller device 32 matching the device key or unique identifier 46 entered will play a sync confirmation tune. The patient being discharged is now linked to this controller device 32.

Medication Regimen Set-Up

The medication regimen for the patient is set-up in the following manner, as shown by FIGS. 8-13. After setting up the patient's controller device 32, the healthcare/medical practitioner proceeds to set up each of the patient's individual medication schedules in healthcare discharge portal 66 by clicking on the "add" button in the patient's detail page. This opens up the "add regimen" form, which is used to create individual medication schedules for the patient. These schedules are stored in cloud network 40 upon submission, and communicated to the controller device 32.

The first field in the "add regimen" form prompts the healthcare/medical practitioner to enter the name of the medication being configured, optionally selecting "other/multiple" for regimens assigned to a multi-medication pack or alternative medication containers 50.

The healthcare/medical practitioner then affixes a new individual set of medication indicia 48 to the container 50 containing the medication specified in the previous step, broadcasting its encrypted unique identifier and color code to controller device 32. This data is sent to cloud network 40 and updates the form display to show that the individual set of medication indicia 48 on container 50 is now linked to this particular regimen. To avoid conflicting individual set of medication indicia 48 broadcasts in a hospital environment with multiple devices being set up, the individual set of medication indicia 48 must be pressed within a certain distance (measured by Bluetooth® signal strength) of the controller device 32 being used, such as, for example, within one foot. The healthcare/medical practitioner then selects the days of the week that the medication should be taken as well as the times of day (up to four) that the reminder should trigger on controller device 32. The healthcare/medical practitioner can also fill out the optional "medication notes" field with dosage notes or other additional information.

In some embodiments, the healthcare/medical practitioner can configure up to six medication regimens with up to six unique indicia such as color codes (red, yellow, green, blue, purple and white) corresponding to the six set of medication indicia 48 colors. After all the medication regimens are configured, the healthcare/medical practitioner gives controller device 32 and containers 50 with attached individual set of medication indicia 48 to take home with instructions to plug the controller device 32 into an outlet 74 in their home that is easily seen and accessible. In some embodiments, the healthcare/medical practitioner can configure from about 1 to about 100 medication regimens with up to 100 unique indicia.

Medication Reminder

After the patient brings controller device 32 back home and plugs it into an outlet 74, controller device 32 will automatically reconnect to cloud network 40 and play the device connected tune and LED light sequence to confirm that it is operational. When it comes time to take a scheduled medication (according to the times of day configured), controller device 32 will turn on the LED light (individual set of medication indicia 42) that matches the color code of the medication scheduled to be taken.

The patient is prompted by the LED and tune sequence to open the container(s) 50 corresponding to the colors lit (individual set of medication indicia 42) on controller device 32 and take their medication. An individual set of medication indicia 48 located on container 50 is depressed and the color code and unique identifier of the individual set of medication indicia 48 will be broadcasted to controller device 32, which will turn off the LED light of that specific color and relay this information to the cloud. If all of the active colors on the device are dismissed, the device will play a reminder complete tune and light sequence as a confirmation.

In some embodiments, the patient has the option to take the medication an hour before the reminder triggers and up to an hour after. Taking the medication after that hour-long window marks the medication as taken late and failing to take the medication before the next reminder marks the medication as missed.

Reminder Volume/Assistance Request

As shown in FIG. 14, engaging button 44 for volume on controller device 32 will cycle through three volume settings, high volume (default setting), low volume, and silent. Holding down the button 44 for three seconds or longer will trigger a confirmation LED blink and buzzer sequence and create an in-app notification in healthcare discharge portal 66 that notifies the care coordinator that the patient needs technical or customer support.

Medication Diary

As shown in FIG. 15, the "medication diary" page in healthcare discharge portal 66 is a feature available for care coordinators who want the specifics of a particular patient's adherence to their medication. This timeline-based view aggregates adherence activity over specific days as well as time periods, providing detailed logs of the patient's usage of the system.

Adherence Status

Patients in healthcare discharge portal 66 can be grouped into four categories based on adherence data collected in the last 30 days. The four categories include as needed, inconsistent, adherent, and disconnected. In some embodiments, as needed medications are not included in these groupings. If the patient misses more than 40% of their doses for any of their scheduled medications, the patient is categorized as non-adherent. If the patient misses between 20% and 40% of their doses for any of their scheduled medications, the patient is categorized as inconsistent. If the patient misses less than 20% of their doses for any of their scheduled medications, the patient is categorized as adherent. If the patient's controller device 32 is not plugged in and/or connected to cloud network 40, the patient is categorized as disconnected.

Non-Adherence Graph

Figure 16:
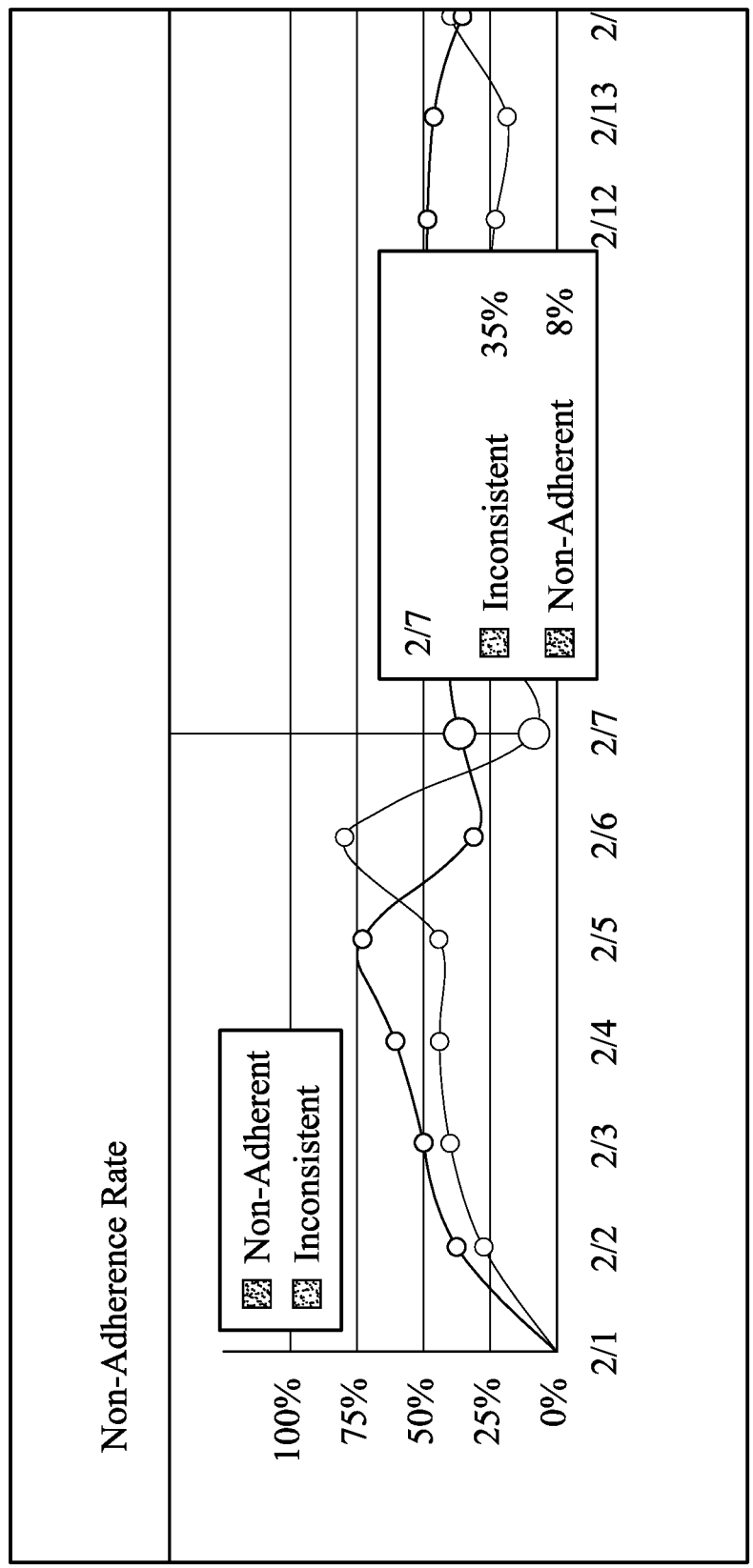
FIG. 16 is a screen shot of a non-adherence rate graph found in the dashboard page of the healthcare discharge portal, illustrating the non-adherence of all patients monitored by the system.

As shown in FIG. 16, a non-adherence rate graph tracks the aggregated distribution of the adherence status of the hospital's entire patient population. This data view is available in the "dashboard" page of healthcare discharge portal 66.

Follow-Up Display

As shown in FIG. 17, clicking on the "follow up" button opens up a popup display that lists the patient's phone number as well as his or her most relevant recent adherence data. Follow-up attempts can be logged and used to clear out the list of patients needing follow up. The "needs follow-up" list is displayed on the "dashboard" page of healthcare discharge portal 66 and consists of a list of patients that need a follow-up call with a care coordinator, based on their adherence status.

Caregiver Controller Device

Figure 19:
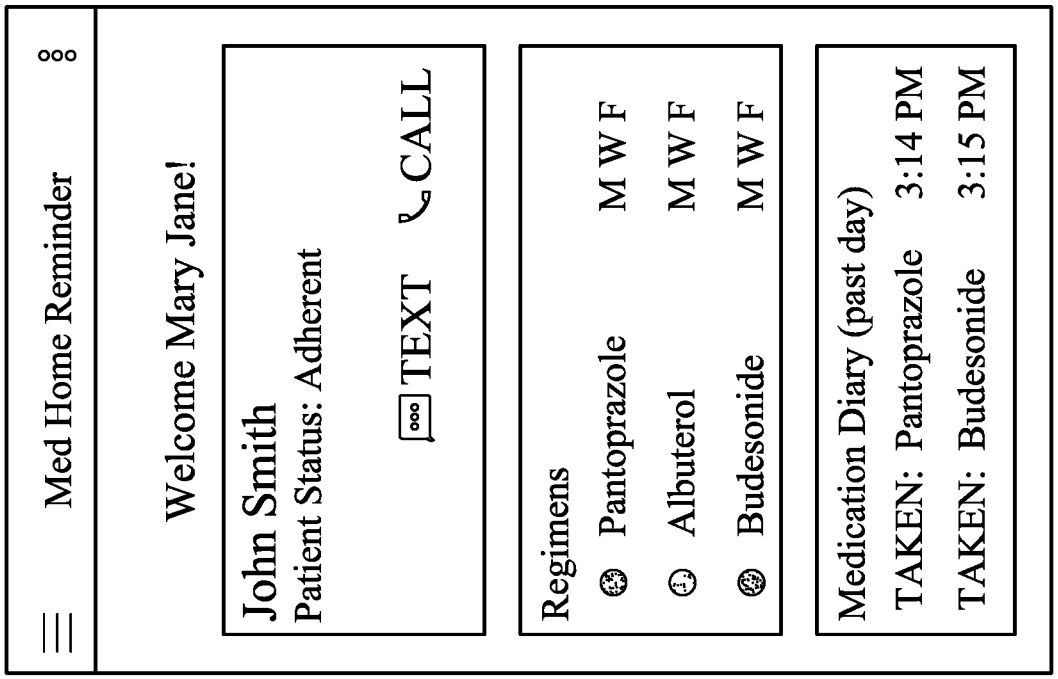
Figure 18:
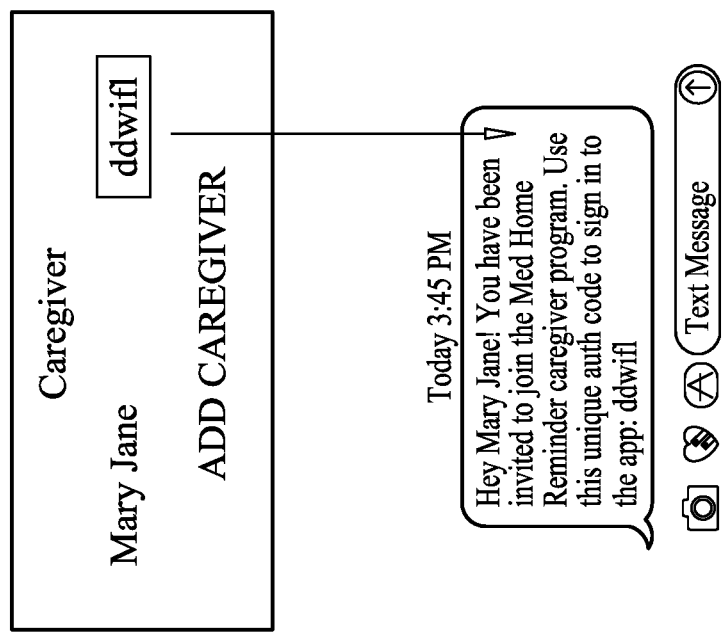
FIG. 18 is a screen shot of the caregiver controller device when a nurse or a caregiver coordinator registers a caregiver.

A healthcare/medical practitioner or care coordinator can register a caregiver with a recently discharged patient in the "patient detail" page. After filling in the caregiver's contact information, a unique six-digit key is generated, sent to the caregiver's mobile phone number via SMS message, and can then be used to login securely to caregiver controller device 68 which is a mobile application, as shown in FIGS. 18 and 19.

Cloud Network

When a healthcare/medical practitioner configures a regimen for a patient in healthcare discharge portal 66, the regimen data is stored along with additional patient data (name, phone number, and device key) in cloud network 40 (e.g., via a network-attached storage device, such as a server). Cloud network 40 manages the medication reminder triggers for each registered controller device 32. When a particular medication is due, the LED status update is sent via the existing cellular connection to each individual controller device 32 which then starts the audio and visual reminders. Based on the patient's medication schedule and individual set of medication indicia 48, cloud network 40 generates adherence data.

Additional Embodiments

Figure 20:
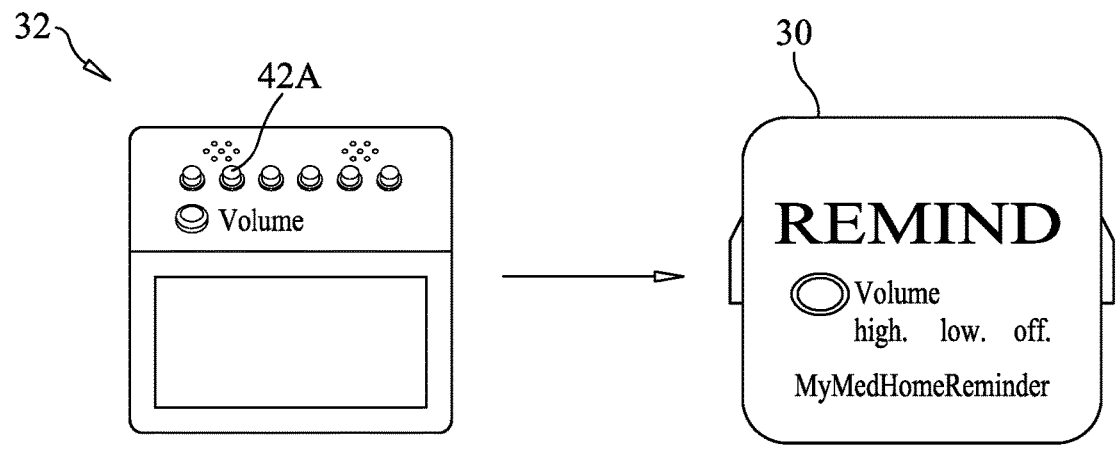
FIG. 20 is a perspective view of embodiments of the controller device component of the system in accordance with the principles of the present disclosure. In one embodiment, the controller device utilizes a color to associate with the medication that has a colored medication indicia affixed to it. In another embodiment, the controller device utilizes a colored letter to associate the medication that has a colored and lettered medication indicia affixed to it.
Figure 21:
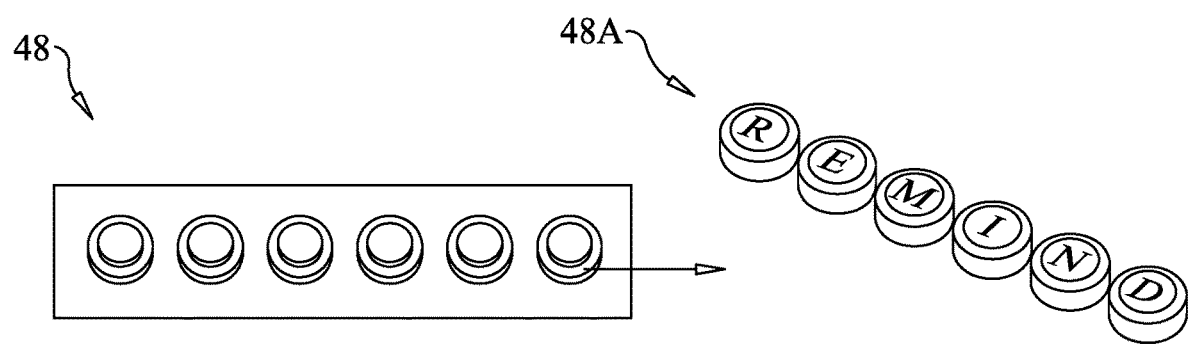
FIG. 21 is a perspective view of embodiments of medication indicia components of the system in accordance with the principles of the present disclosure. In one embodiment, the medication indicia utilize a color to associate with the medication. In another embodiment, the medication indicia utilizes a colored letter to associate with the medication.

In some embodiments, as shown in FIGS. 20 and 21, medication reminder system 30 is modified to address color blindness. Each set of medication indicia 42A of controller device 32 comprises a letter code scheme that enables colorblind patients to utilize medication reminder system 30 since a letter can be seen in addition to a color. Each set of medication indicia 48A comprises the same letters associated with each set of medication indicia 42A. Controller device 32 via set of medication indicia 42A therefore displays a colored letter that is associated with a container 50 that has affixed to it an individual set of medication indicia 48A, which has the same color and letter.

In some embodiments, instead of using any set of letters, a word related that to the product can be spelled and the word used cannot contain the same letter more than once, such as, the word "remind."

Figure 25:
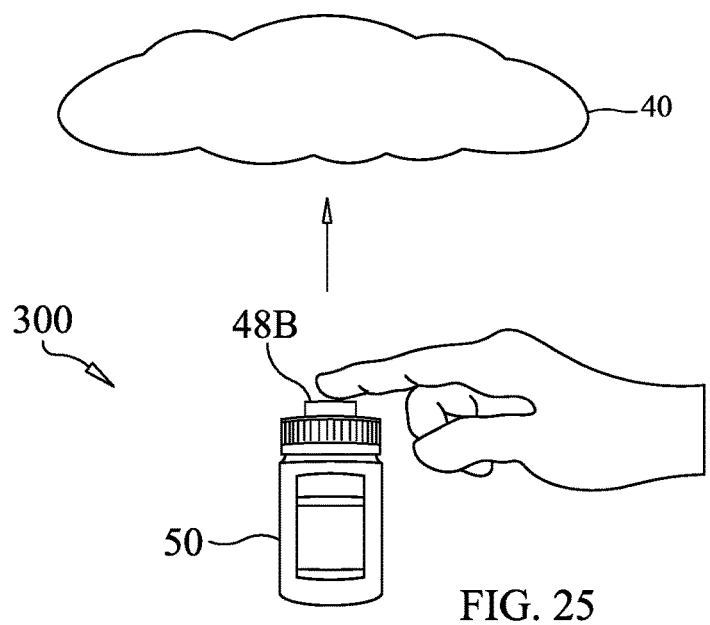
FIG. 25 is a front view of components of one embodiment of a system in accordance with the principles of the present disclosure.

In some embodiments, as shown in FIG. 25, medication reminder system 300, similar to medication reminder system 30 as described above, includes a medication indicia 48B. Medication indicia 48B comprises a transceiver operable to transmit and receive data to provide or generate input data representing confirmation of adherence to a dosage regimen. Medication indicia 48B is configured to function in a similar manner to controller device 32, as described above.

Medication indicia 48B is configured to contact a container 50 having the medication disposed within container 50. In some embodiments, medication indicia 48B adheres to container 50. In some embodiments, medication indicia 48B does not adhere to container 50 and alternatively is next to or near container 50. Medication indicia 48B is operable to display an indicator representing the dosage regimen or a parameter associated with the dosage regimen. In some embodiments, medication indicia 48B can blink an LED light and/or a buzzer tune can be played when it is time for a scheduled medication to be taken. When medication indicia 48B is pressed, it acknowledges that the medication has been taken and this data is then transmitted back to cloud network 40 and cloud network 40 then transmits the data to computer 70. Input data is then provided or generated that represents a confirmation of adherence to the dosage regimen to computer 70 and/or set of medication indicia 48B. Medication reminder system 300 additionally includes all of the features of medication reminder system 30 except for controller device 32.

Figure 26:
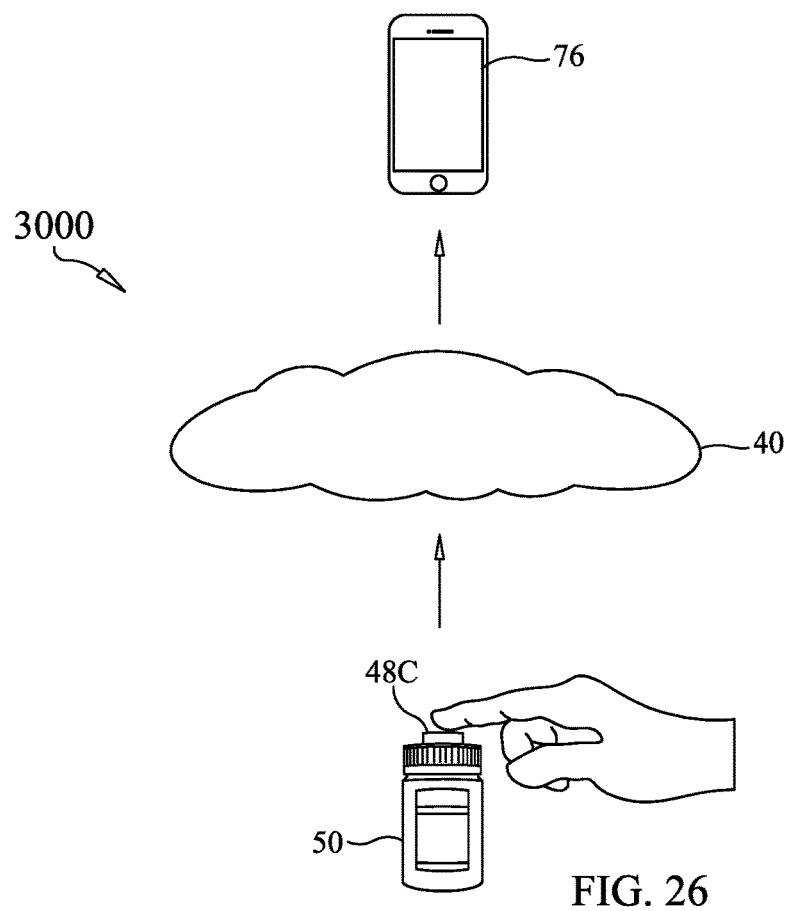
FIG. 26 is a schematic view of components of one embodiment of a system in accordance with the principles of the present disclosure.

In some embodiments, as shown in FIG. 26, medication reminder system 3,000, similar to medication reminder system 30 as described above, includes a computer comprising a tablet computer or a smartphone 76. Smartphone 76 is operable to transmit and receive data representing a dosage regimen for the medication for use with a medication indicia 48C. Smartphone 76 is configured to function in a similar manner to controller device 32, as described above. In some embodiments, smartphone 76 replaces controller device 32. Smartphone 76 functions like controller device 32 via a computer application.

Medication indicia 48C is similar to medication indicia 48 and is configured to contact a container 50 having the medication disposed within container 50. Medication indicia 48C sends data/transmissions to smartphone 76 to provide or generate input data representing confirmation of adherence to the dosage regimen.

Similar to medication reminder system 30, medication reminder system 3,000 further comprises a healthcare discharge portal web application 66 with a medication regimen setup and adherence tracking features for hospitals, a smartphone application with patient monitoring and adherence tracking features for caregivers, and cloud network 40 that performs as a scheduling engine and database for managing medication regimens and reminders for users of the medication reminder system.

Figure 27:
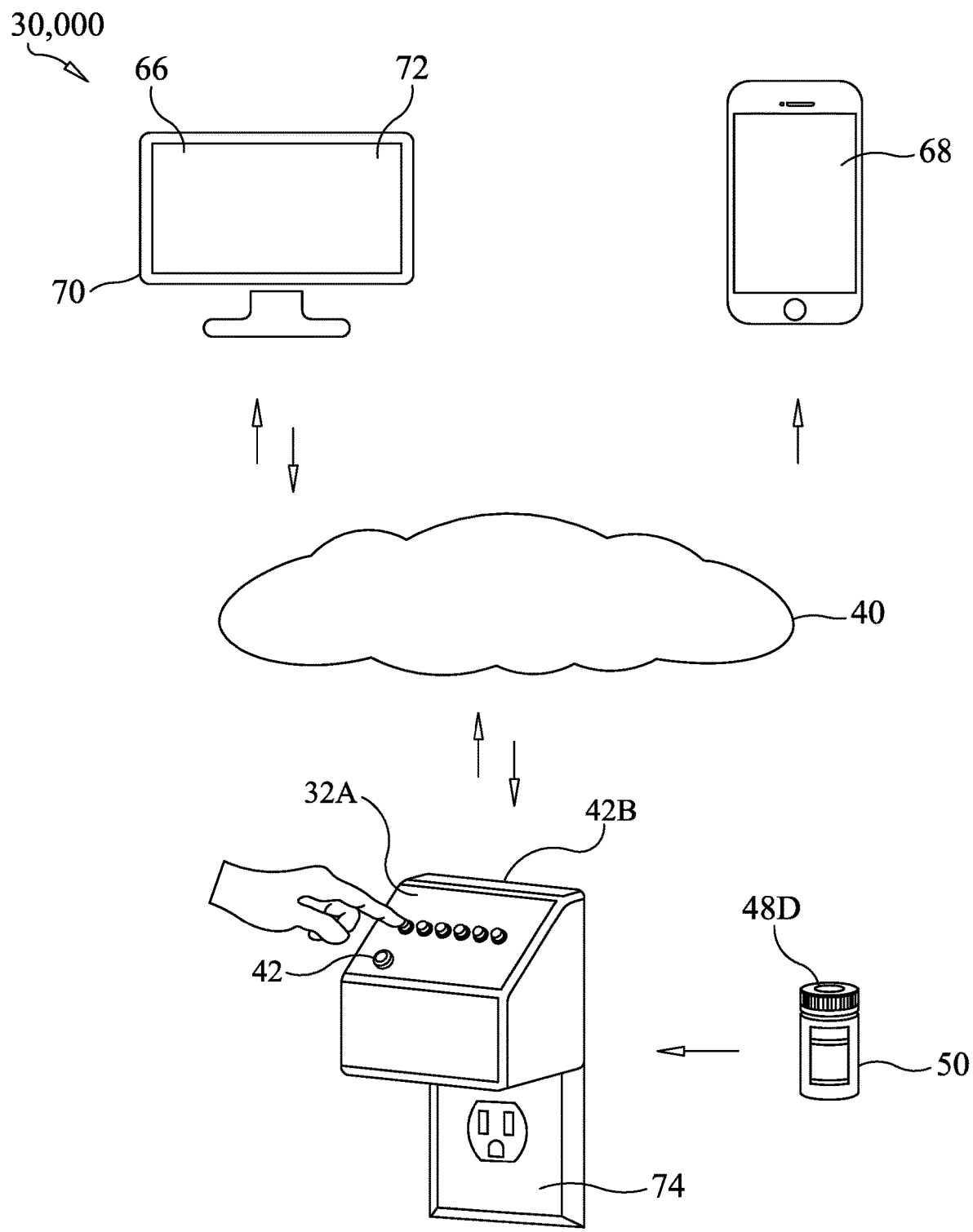
FIG. 27 is a schematic view of components of one embodiment of a system in accordance with the principles of the present disclosure.

In some embodiments, as shown in FIG. 27, medication reminder system 30,000, similar to medication reminder system 30 as described above, includes a controller device 32A operable to provide or generate input data representing confirmation of adherence to a dosage regimen for use with a medication indicia 48D. Controller device 32A performs in a similar manner to controller device 32 combined with medication indicia 48. Medication indicia 48D is configured to contact a container 50 having the medication disposed within container 50. Medication indicia 48D is a sticker. Controller device 32A is operable to display an indicator, indicators, a medication indicia or a set of medication indicia 42B representing the dosage regimen or a parameter associated with the dosage regimen. In some embodiments, medication indicia 42B is a colored LED light that is an identical color to medication indicia 48D. When it is time for a scheduled medication to be taken, the colored LED light of medication indicia 42B blinks, alerting the patient to take the medication associated with the color of the LED light. When medication indicia 42B is pressed, it acknowledges that the medication has been taken and this data is then transmitted back to cloud network 40 and cloud network 40 then transmits the data to computer 70. Input data is then provided or generated that represents a confirmation of adherence to the dosage regimen to computer 70 and/or set of medication indicia 42B.

As-Needed Medications

Figures 22, 23:
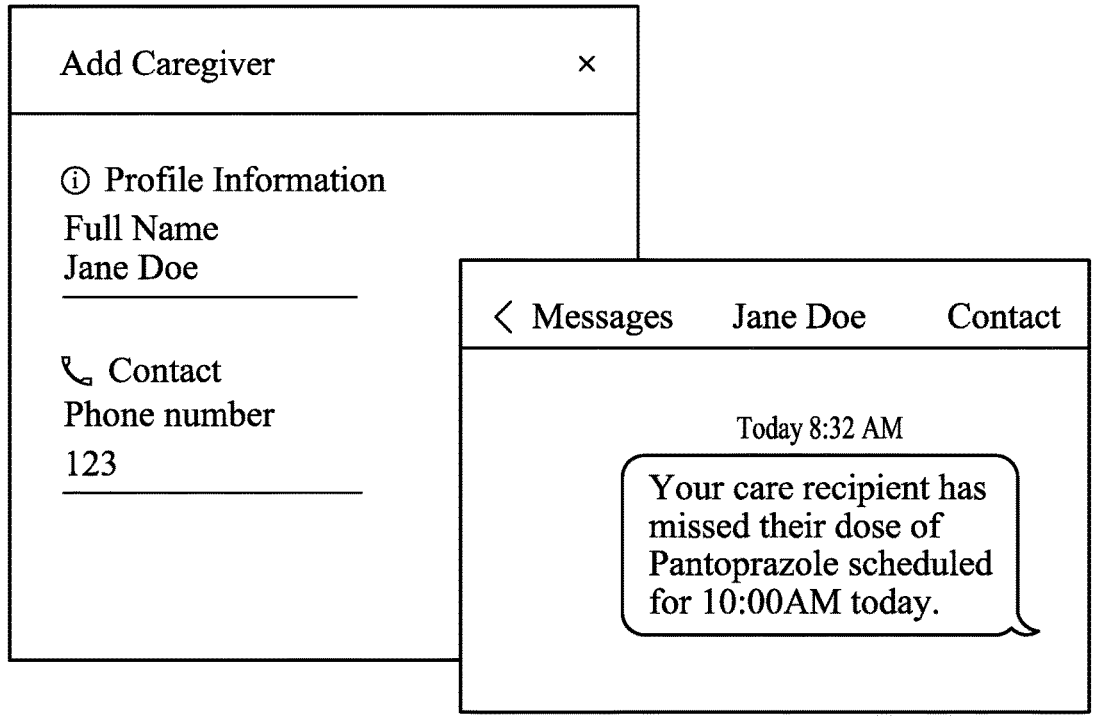
FIG. 22 is a screen shot of the healthcare discharge portal showing as-needed medication synched with a medication indicia.
FIG. 23 is a screen shot of a caregiver notification system showing that a non-professional caregiver can be added to the patient's profile, and shows an automated text messaging service which allows notifications to be sent when a patient misses a scheduled medication dose.

In some embodiments as shown in FIG. 22, medication reminder system 30 can support medications that are taken as-needed (PRN) and individual set of medication indicia associated with as-needed medications can be black or grey. These color indicators can be set up in healthcare discharge portal 66 and can record when the patient takes a dose of an unscheduled as-needed medication. These recordings are separately reconciled and are viewable in the patient's medication diary but are not factored into calculations involving the patient's overall adherence to their medication.

Set Duration Medications

In some embodiments, medication reminder system 30 supports setting a custom duration (from 1 to 30 days) for a specific medication reminder. This distinction can be configured during initial medication set-up. After the specified duration, the reminder-scheduling algorithm discontinues future medication reminders for that particular medication.

Adherence Status Grouping

In some embodiments, medication reminder system 30 can group patients into three overall adherence categories such as non-adherent, inconsistent, and adherent. Medication reminder system 30 processes the patient's adherence data daily and algorithmically identifies the medication with the lowest adherence rate based on a boxcar average of the last seven days (or less if seven days' worth of data has not yet been generated) of adherence data (not including as-needed medications). This adherence rate is then used to group the patient. If the patient misses more than 40% of their doses for any of their scheduled medications, the patient is categorized as non-adherent. If the patient misses between 20% and 40% of their doses for any of their scheduled medications, the patient is categorized as inconsistent. If the patient misses less than 20% of their doses for any of their scheduled medications, the patient is categorized as adherent.

Adherence Data Reconciliation

In some embodiments, medication reminder system 30 performs advanced adherence data reconciliation on the raw data transmitted by each patient's individual set of medication indicia 48. This reconciliation algorithm accommodates a variety of adherence scenarios, including when the patient takes their medication early, when they take their medication after a reminder has expired, and when controller device 32 is disconnected from the cellular network. Every time the individual set of medication indicia 48 transmits a button 44 press, this data is cross-checked with the patient's configured medication regimen and reminder schedule to create a medication diary entry with one of the categorizations such as, taken, taken late, missed, unknown, and as-needed.

Caregiver Notifications

In some embodiments, as shown in FIG. 23, a caregiver notification system is added to medication reminder system 30 that allows non-professional caregivers to be added to the patient's profile, enrolling them in an automated text messaging (SMS) service wherein the caregiver can elect to receive notifications whenever their care recipient misses a scheduled medication dose.

Adherence Monitoring Disconnected Notification

In some embodiments, as shown in FIG. 24, a disconnected notification can be added to medication reminder system 30 to inform the hospital staff users of healthcare discharge portal 66 of managed patients whose controller devices 32 are disconnected from the cellular network and are therefore unable to receive medication reminders. This notification is automatically generated by medication reminder system 30 for each patient when the following two conditions are matched: (1) the patient has a scheduled medication due in the next 30 minutes, and (2) the patient's controller device 32 is currently disconnected from the network. This feature prompts hospital staff to call the affected patients and either resolve the connection issue or manually remind the patient to take their medication and mark the reminder as "TAKEN."

Container and Medications

Container 50 can be any container used to dispense a medication. For example, container 50 can be a blister package, an injectable container such as a syringe, an inhaler, a vial, and/or a bottle. The medication disposed within container 50 can comprise at least one of a capsule, tablet, mini-tablet, caplet, solution, suspension, ointment, cream, inhaler, spray, drop, patch, or an injection. In some embodiments, the medication can include, such as, for example, a chewable tablet, quick dissolve tablet, effervescent tablet, reconstitutable powder, elixir, liquid, solution, suspension, emulsion, tablet, multi-layer tablet, bi-layer tablet, capsule, soft gelatin capsule, hard gelatin capsule, caplet, lozenge, chewable lozenge, bead, powder, granules, dispersible granules, cachets, douche, suppository, cream, topical, inhalant, aerosol inhalant, patch, particle inhalant, implant, depot implant, dragee, ampoule, ingestible, injectable, infusion, health bar, liquid, food, nutritive food, functional food, yogurt, gelatin, cereal, cereal coating, animal feed and/or combinations thereof.

In some embodiments, the medication may comprise vitamin A, B vitamins, vitamin C, vitamin D, vitamin E, vitamin K, essential fatty acids, folic acid, iron, calcium, magnesium, potassium, copper, chromium, zinc, molybdenum, iodine, boron, selenium, manganese, derivatives thereof and/or combinations thereof. In some embodiments, the medication may include biologically-active substances may include thiamin, thiamin pyrophosphate, riboflavin, flavin mononucleotide, flavin adenine dinucleotide, niacin, nicotinic acid, nicotinamide, niacinamide, nicotinamide adenine dinucleotide, tryptophan, biotin, folic acid, pantothenic acid, ascorbic acid, retinol, retinal, retinoic acid, beta-carotene, 1,25-dihydroxycholecalciferol, 7-dehyrdocholesterol, alpha-tocopherol, tocopherol, tocotrienol, menadione, menaquinone, phylloquinone, naphthoquinone, calcium, calcium carbonate, calcium sulfate, calcium oxide, calcium hydroxide, calcium apatite, calcium citrate-malate, calcium gluconate, calcium lactate, calcium phosphate, calcium levulinate, phosphorus, potassium, sulfur, sodium, docusate sodium, chloride, magnesium, magnesium stearate, magnesium carbonate, magnesium oxide, magnesium hydroxide, magnesium sulfate, copper, iodine, zinc, chromium, molybdenum, carbonyl iron, ferrous fumarate, polysaccharide iron, and/or combinations and derivatives thereof.

In some embodiments, the medication may be prescription and/or non-prescription substances. In some embodiments, the prescription substance may be a hormone replacement agent, a contraceptive agent, an osteoporotic agent, a chemotherapeutic agent, an anti-infective agent, analgesic, a steroid, an appetite suppressant, a weight loss agent, a tobacco antagonist, a cholesterol reducer and/or combinations thereof.

In some embodiments, the prescription substances may include, such as, for example, ticagrelor (anti-platelet), clopidogrel (anti-platelet), prasugrel (anti-platelet), carvedilol (beta blocker), metoprolol succinate (beta blocker), metoprolol tartrate (beta blocker), lisinopril (ACE inhibitor), losartan (angiotensin receptor blocker), valsartan (angiotensin receptor blocker), atorvastatin (statin), simvastatin (statin), spironolactone (aldosterone receptor blocker/diuretic), atenolol, erythromycin, penicillins, cephalosporins, theophylline, albuterol, terbutaline, diltiazem, propranolol, nifedepine, clonidine, thioridazine, diazepam, meclizine, ergoloid mesylates, chlorpromazine, carbidopa, levodopa, beclomethasone diproprionate, budesonide, dexamehasone, flunisolide, fluticasone proprionate, mometasone furoate, triamcinolone acetonide, beconase, pulmicort, rhinocort, decadron, aerobid/nasolide, flovent/flonase, azmacort, amprenavir, adefovir dipivoxil, zidovudine, azidothymidine, AZT, paclitaxel, cyclophosphamide, teniposide, taxol, cytoxan, vumon, methotrexate, methotrexate, cisplatin, carboplatin, oxaliplatin, platinol, paraplatin, adriamycin, bleomycin, dactinomycin, daunorubicin, doxorubicin, indarubicin, mitomycin, blenoxane, cosmegen, cerubidine, rubex, indamycin, mutamycin, BCNU, streptozocin, vinblastine, thiotepa, conjugated estrogens, esterified estrogens, estropipate, estradiol, ethinyl estradiol, medroxyprogesterone, meprobamate, desogestrel, levonorgestrel, norethindrone, norethindrone acetate, norgestimate, norgestrel, raloxifene, tamoxifen, methyltestosterone, quinapril, sotalol, alendronate, atorvastatin, colestipol, clofibrate, and/or combinations thereof.

In some embodiments, the non-prescription substance can be a vitamin or derivative thereof, and/or a mineral compound or derivative thereof. In some embodiments, the vitamin or mineral compound may be, such as, for example, thiamin, thiamin pyrophosphate, riboflavin, flavin mononucleotide, flavin adenine dinucleotide, niacin, nicotinic acid, nicotinamide, niacinamide, nicotinamide adenine dinucleotide, tryptophan, biotin, folic acid, pantothenic acid, ascorbic acid, retinol, retinal, retinoic acid, beta-carotene, 1,25-dihydroxycholecalciferol, 7-dehydrocholesterol, alpha-tocopherol, tocopherol, tocotrienol, menadione, menaquinone, phylloquinone, naphthoquinone, calcium, calcium carbonate, calcium sulfate, calcium oxide, calcium hydroxide, calcium apatite, calcium citrate-malate, calcium gluconate, calcium lactate, calcium phosphate, calcium levulinate, phosphorus, potassium, sulfur, sodium, docusate sodium, chloride, magnesium, magnesium stearate, magnesium carbonate, magnesium oxide, magnesium hydroxide, magnesium sulfate, copper, iodine, zinc, chromium, molybdenum, carbonyl iron, ferrous fumarate, polysaccharide iron, and combinations and derivatives thereof. In some embodiments, the derivatives of vitamin compounds include salts, alkaline salts, esters and chelates of any vitamin compound. In some embodiments, the nonprescription substance can be a herbal compound, herbal extract, derivative thereof and/or combinations thereof.

Methods

A computer-implemented method for providing a medication reminder is provided, the method comprising transmitting and receiving data representing a dosage regimen for the medication at a controller device for use with a medication indicia, the medication indicia configured to contact a container having the medication disposed within the container, the medication indicia including a transceiver operable to send and receive data to and from the controller device; transmitting the data representing a dosage regimen for the medication from the controller device to the medication indicia; and providing or generating input data representing confirmation of adherence to the dosage regimen to the controller device and/or medication indicia.

In some embodiments, the controller device is operable to receive and transmit data to a healthcare discharge portal or a caregiver controller device. The medication indicia comprise an adhesive to contact the container having medication disposed therein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A medication reminder system, the medication reminder system comprising:
    a controller device operable to receive data representing a dosage regimen for medication involved in a medication regimen for a patient; and
    a plurality of medication indicia, each medication indicia of the plurality of medication indicia configured to contact a container, each medication indicia of the plurality of medication indicia including a wireless transmitter operable to send data representing confirmation of adherence to the dosage regimen by the patient to the controller device;
    wherein the controller device is operable to:
        display a first indicator associated with the dosage regimen based on receiving the data representing confirmation of adherence to the dosage regimen by the patient from a wireless transmitter of a first medication indicia of the plurality of medication indicia;
        display a second indicator associated with the dosage regimen based on receiving the data representing confirmation of adherence to the dosage regimen by the patient from a wireless transmitter of a second medication indicia of the plurality of medication indicia; and
        wherein the first indicator is different from the second indicator.

2. The medication reminder system of claim 1, wherein the controller device is operable to wirelessly transmit data to a healthcare discharge portal or a caregiver controller device.

3. The medication reminder system of claim 1, wherein each medication indicia of the plurality of medication indicia comprises an adhesive to contact a container having medication disposed therein.

4. The medication reminder system of claim 1, wherein each medication indicia of the plurality of medication indicia has unique indicia, wherein the unique indicia comprises at least one color, letter, sound, light and/or video.

5. The medication reminder system of claim 2, wherein the controller device is operable via a cloud network.

6. The medication reminder system of claim 1, wherein the container comprises an inhaler.

7. The medication reminder system of claim 1, wherein the plurality of medication indicia are a first plurality of medication indicia, and wherein the controller device comprises a second plurality of medication indicia that is paired to the first plurality of medication indicia using a unique identifier.

8. The medication reminder system of claim 1, wherein each medication indicia of the plurality of medication indicia is an electronic button.

9. A computer-implemented method for providing a medication reminder, the method comprising:
    transmitting, with a wireless transmitter of a first medication indicia, first data representing a dosage regimen for medication involved in a medication regimen for a patient to a controller device, the first medication indicia configured to contact a container wherein the first data representing the dosage regimen comprises first data representing confirmation of adherence to the dosage regimen by the patient; and
    transmitting, with a wireless transmitter of a second medication indicia, second data representing the dosage regimen to the controller device, the second medication indicia configured to contact a container, wherein the second data representing the dosage regimen comprises second data representing confirmation of adherence to the dosage regimen by the patient;
    displaying, with the controller device, a first indicator representing the dosage regimen or a parameter associated with the dosage regimen based on receiving the first data representing confirmation of adherence to the dosage regimen by the patient from the wireless transmitter of the first medication indicia; and
    displaying, with the controller device, a second indicator representing the dosage regimen or a parameter associated with the dosage regimen based on receiving the second data representing confirmation of adherence to the dosage regimen by the patient from the wireless transmitter of the second medication indicia;
    wherein the first indicator is different from the second indicator.

10. The computer-implemented method of claim 9, further comprising:
    wirelessly transmitting data to a healthcare discharge portal or a caregiver controller device.

11. The computer-implemented method of claim 9, wherein the first medication indicia comprises an adhesive to contact the container.

12. A medication reminder system, the medication reminder system comprising:
    a controller device;
    a plurality of adhesive medication indicia;
    a healthcare discharge portal web application with a medication regimen setup and adherence tracking features for hospitals;
    a caregiver controller device comprising a smartphone application with patient monitoring and adherence tracking features for caregivers; and
    a cloud network that performs as a scheduling engine and database for managing medication regimens and reminders for users of the medication reminder system;
    wherein the controller device is operable to communicate with the cloud network via a cellular network and the controller device is operable to wirelessly transmit data to the healthcare discharge portal and the caregiver controller device;

wherein the controller device is operable to:
  display a first indicator associated with a dosage regimen for a medication involved in a medication regimen for a patient based on receiving data representing confirmation of adherence to the dosage regimen by the patient from a wireless transmitter of a first medication indicia of the plurality of adhesive medication indicia; and
  display a second indicator associated with the dosage regimen based on receiving the data representing confirmation of adherence to the dosage regimen by the patient from a wireless transmitter of a second medication indicia of the plurality of adhesive medication indicia;
  wherein the first indicator is different from the second indicator.

13. A medication reminder system, the system comprising:
  a controller device operable to receive data including a dosage regimen for medication involved in a medication regimen for a patient, the controller device having a display comprising a first medication indicia, the first medication indicia representing the dosage regimen or a parameter associated with the dosage regimen; and
  a second medication indicia including a wireless transmitter operable to send data to the controller device, the second medication indicia corresponding to the dosage regimen or the parameter associated with the dosage regimen of the first medication indicia, and the second medication indicia being paired to the first medication indicia,
  wherein the second medication indicia is configured to contact a container having the medication disposed within the container;
  wherein the controller device is operable to:
  display a first indicator associated with the dosage regimen on the first medication indicia based on receiving data representing confirmation of adherence to the dosage regimen by the patient to the dosage regimen from the wireless transmitter of the second medication indicia.

14. The medication reminder system of claim 13, wherein the second medication indicia comprises an electronic button having an adhesive to contact the container.

15. The medication reminder system of claim 13, wherein the first medication indicia corresponds to a particular medication and the second medication indicia corresponds to the particular medication, and the parameter associated with the dosage regimen is at least one of a name of the particular medication, a time interval for administering the particular medication, a strength of the particular medication, a dosing frequency of the particular medication, a dosage form of the particular medication, a route of administration of the particular medication, a patient name or an alert for the particular medication.

16. The medication reminder system of claim 13, wherein the first medication indicia is paired to the second medication indicia using a unique identifier.

17. The medication reminder system of claim 13, wherein the first medication indicia and/or the second medication indicia comprises at least one color, letter, sound, light and/or video.

18. The medication reminder system of claim 16, wherein the first medication indicia is wirelessly paired to the second medication indicia using the unique identifier.

19. The medication reminder system of claim 1, wherein the controller device comprises a plug configured to fit into a power outlet.

* * * * *